(12) United States Patent
Andreotti et al.

(10) Patent No.: US 7,790,758 B2
(45) Date of Patent: Sep. 7, 2010

(54) COMPOUNDS WHICH POTENTIATE GLUTAMATE RECEPTOR AND USES THEREOF IN MEDICINE

(75) Inventors: Daniele Andreotti, Verona (IT); Luca Arista, Verona (IT); Francesca Cardullo, Verona (IT); Simone Spada, Verona (IT); Kevin Michael Thewlis, Harlow (GB); Simon Edward Ward, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 588 days.

(21) Appl. No.: 11/816,284

(22) PCT Filed: Feb. 13, 2006

(86) PCT No.: PCT/EP2006/001342

§ 371 (c)(1),
(2), (4) Date: Aug. 15, 2007

(87) PCT Pub. No.: WO2006/087169

PCT Pub. Date: Aug. 24, 2006

(65) Prior Publication Data

US 2008/0167351 A1    Jul. 10, 2008

(30) Foreign Application Priority Data

Feb. 15, 2005  (GB) ................... 0503155.4
Jan. 26, 2006  (GB) ................... 0601612.5

(51) Int. Cl.
| | | |
|---|---|---|
| C07D 333/20 | (2006.01) | |
| C07D 317/58 | (2006.01) | |
| C07D 277/64 | (2006.01) | |
| C07D 213/61 | (2006.01) | |
| C07D 213/42 | (2006.01) | |
| C07D 213/647 | (2006.01) | |
| C07D 213/64 | (2006.01) | |
| C07D 213/65 | (2006.01) | |
| C07C 311/08 | (2006.01) | |
| A61K 31/4418 | (2006.01) | |
| A61K 31/428 | (2006.01) | |
| A61K 31/381 | (2006.01) | |
| A61K 31/36 | (2006.01) | |
| A61K 31/277 | (2006.01) | |
| A61K 31/18 | (2006.01) | |

(52) U.S. Cl. ............. 514/357; 514/605; 514/524; 514/466; 514/438; 514/465; 514/351; 514/367; 546/300; 546/338; 548/179; 549/75; 549/443; 558/418; 564/99

(58) Field of Classification Search ................ None
See application file for complete search history.

(56) References Cited

U.S. PATENT DOCUMENTS

2005/0222146 A1 * 10/2005 Fryer et al. ............. 514/232.2
2007/0270471 A1 * 11/2007 Thewlis et al. ............. 514/343

* cited by examiner

Primary Examiner—Rebecca L Anderson
Assistant Examiner—Matthew P Coughlin
(74) Attorney, Agent, or Firm—James M. Kanagy; Edward R. Gimmi; Charles M. Kinzig

(57) ABSTRACT

This invention relates to potentiation of the glutamate receptor by novel compounds of formula (I):

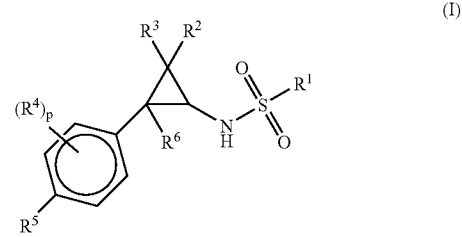

The invention also relates to the use of the derivatives in treating diseases and conditions mediated by potentiation of the glutamate receptor, compositions containing the derivatives and processes for their preparation.

15 Claims, No Drawings

COMPOUNDS WHICH POTENTIATE GLUTAMATE RECEPTOR AND USES THEREOF IN MEDICINE

This application is a 35 U.S.C. 371 application of International Application No. PCT/EP2006/001342, filed 13 Feb. 2006, and which claims the benefit of Provisional Application No. GB0503155.4, filed 15 Feb. 2005.

This invention relates to novel compounds which potentiate the glutamate receptor. The invention also relates to the use of the compounds in treating diseases and conditions mediated by potentiation of the glutamate receptor, compositions containing the derivatives and processes for their preparation.

Glutamate receptors, which mediate the majority of fast excitatory neurotransmission in the mammalian central nervous system (CNS), are activated by the excitatory amino acid, L-glutamate (for review see Watkins J C, Krogsgaard-Larsen P, Honore T (1990) Trends Pharmacol Sci 11: 25-33).

Glutamate receptors can be divided into two distinct families. The G-protein or second messenger-linked "metabotropic" glutamate receptor family which can be subdivided into three groups (Group I, mGlu1 and mGlu5; Group II, mGlu2 and mGlu3; Group III, mGlu4, mGlu6, mGlu7, mGlu8) based on sequence homology and intracellular transduction mechanisms (for review see Conn P J and Pinn J P (1997) Ann Rev Pharmacol Toxicol 37: 205-237). The "ionotropic" glutamate receptor family, which directly couple to ligand-gated cation channels, can be subdivided into at least three subtypes based on depolarizing activation by selective agonists, N-methyl-D-aspartate (NMDA), α-amino-3-hydroxy-5-methylisoxazole-4-propionic acid (AMPA) and kainic acid (KA) (for review see Dingledine R, Borges K, Bowie, Traynelis S (1999) 51: 7-61).

Native AMPA receptors (AMPAR) exist as heterotetramers consisting of combinations of four different protein subunits (GluR1-4) (for review see Bettler B and Muller C (1995) 34: 123-139.). Receptor subunit diversity is increased further as each subunit can undergo alternative splicing of a 38 amino acid sequence in the extracellular region just before the fourth membrane spanning domain M4. Such editing results in so-called 'flip' and 'flop' receptor isoforms which differ in kinetic and pharmacological properties (Sommer B, Keinanen K, Verdoon T A, Wisden W, Burnashev N, Herb A, Kohler M, Takagi T, Sakmann B, Seeburg P H (1990) Science 249: 1580-1585).

Additionally, post-transcriptional editing of GluR2 mRNA changes a neutral glutamine to a positively charged arginine within M2. In normal humans >99% GluR2 is edited in this way. AMPAR containing such edited GluR2 subunit exhibit low calcium permeability (Burnachev N, Monyer H, Seeburg P H, Sakmann B (1992) Neuron 8: 189-198). There is a suggestion, however, that the number of AMPAR with high calcium permeability is elevated in certain disease-associated conditions (Weiss J H, and Sensi S L (2000) Trends in Neurosci 23: 365-371).

AMPAR depolarization removes voltage dependent $Mg^{2+}$ block of NMDA receptors which in turn leads to NMDA receptor activation, an integral stage in the induction of LTP (Bliss T V P, Collingridge G L (1993) Nature 361: 31-9). LTP is a physiological measure of increased synaptic strength following a repetitive stimulus or activity, such as occurs during learning.

Direct activation of glutamate receptors by agonists, in conditions where glutamate receptor function is reduced, increases the risk of excitotoxicity and additional neuronal damage. AMPAR positive allosteric modulators do not activate the receptor directly. However, when the ligand (L-glutamate or AMPA) is present AMPAR modulators increase receptor activity. Thus, AMPA receptor modulators enhance synaptic function when glutamate is released and is able to bind at post-synaptic receptor sites.

Compounds which act as AMPAR positive allosteric modulators have been shown to increase ligand affinity for the receptor (Arai A, Guidotti A, Costa E, Lynch G (1996) Neuroreport. 7: 2211-5.); reduce receptor desensitization and reduce receptor deactivation (Arai A C, Kessler M, Rogers G, Lynch G (2000) 58: 802-813) and facilitate the induction of LTP both in vitro (Arai A, Guidotti A, Costa E, Lynch G (1996) 7: 2211-5.) and in vivo (Staubli U, Perez Y, Xu F, Rogers G, Ingvar M, Stone-Elander S, Lynch G (1994) Proc Natl Acad Sci 91: 11158-11162). Such compounds also enhance the learning and performance of various cognitive tasks in rodent (Zivkovic I, Thompson D M, Bertolino M, Uzunov D, DiBella M, Costa E, Guidotti A (1995) JPET 272: 300-309, Lebrun C, Pilliere E, Lestage P (2000) Eu J Pharmacol 401: 205-212), sub-human primate (Thompson D M, Guidotti A, DiBella M, Costa E (1995) Proc Natl Acad Sci 92: 7667-7671) and man (Ingvar M, Ambros-Ingerson J, Davis M, Granger R, Kessler M, Rogers G A, Schehr R S, Lynch G (1997) Exp Neurol 146: 553-559).

It is envisaged that compounds that modulate glutamate receptor function may be useful in treating the following conditions and diseases: psychosis and psychotic disorders (including schizophrenia, schizo-affective disorder, schizophreniform diseases, brief reactive psychosis, child onset schizophrenia, "schizophrenia-spectrum" disorders such as schizoid or schizotypal personality disorders, acute psychosis, alcohol psychosis, drug-induced psychosis, autism, delerium, mania (including acute mania), manic depressive psychosis, hallucination, endogenous psychosis, organic psychosyndrome, paranoid and delusional disorders, puerperal psychosis, and psychosis associated with neurodegenerative diseases such as Alzheimer's disease); cognitive impairment (e.g. the treatment of impairment of cognitive functions including attention, orientation, memory (i.e. memory disorders, amnesia, amnesic disorders and age-associated memory impairment) and language function, and including cognitive impairment as a result of stroke, Alzheimer's disease, Aids-related dementia or other dementia states, as well as other acute or sub-acute conditions that may cause cognitive decline such as delirium or depression (pseudodementia states) trauma, aging, stroke, neurodegeneration, drug-induced states, neurotoxic agents), mild cognitive impairment, age related cognitive impairment, autism related cognitive impairment, Down's syndrome, cognitive deficit related to psychosis, post-electroconvulsive treatment related cognitive disorders; anxiety disorders (including generalised anxiety disorder (GAD), social anxiety disorder (SAD), agitation, tension, social or emotional withdrawal in psychotic patients, panic disorder, and obsessive compulsive disorder); neurodegenerative diseases (such as Alzheimer's disease, ALS, motor neurone disease and other motor disorders such as Parkinson's disease (including relief from locomotor deficits and/or motor disability, including slowly increasing disability in purposeful movement, tremors, bradykinesia, hyperkinesia (moderate and severe), akinesia, rigidity, disturbance of balance and co-ordination, and a disturbance of posture), dementia in Parkinson's disease, dementia in Huntington's disease, neuroleptic-induced Parkinsonism and tardive dyskinesias, neurodegeneration following stroke, cardiac arrest, pulmonary bypass, traumatic brain injury, spinal cord injury or the like, and demyelinating diseases such as multiple sclerosis and amyotrophic lateral sclerosis); depression (which term includes bipolar (manic) depression (including type I and type II), unipolar depression, single or recurrent major depressive episodes with or without psychotic features, catatonic features, melancholic features, atypical features (e.g. lethargy, over-eating/obesity, hypersomnia) or postpartum onset, seasonal affective disorder and dysthymia, depression-related anxiety, psychotic depression, and depressive disorders resulting from a general medical condition including, but not limited to, myocardial infarction, diabetes, miscarriage or abortion); post-traumatic stress syndrome; attention deficit disorder; attention deficit hyperactivity disorder; drug-induced (phencyclidine, ketamine and other dissociative anaesthetics, amphetamine and other psychostimulants and cocaine) disorders; Huntingdon's chorea; tardive dyskinesia; dystonia; myoclonus; spasticity; obesity; stroke; sexual dysfunction; and sleep disorders. The compounds may also be useful in the treatment of some forms of epilepsy. In addition, it is envisaged that compounds that modulate glutamate receptor function may be useful in treating non-impaired subjects for enhancing performance in sensory-motor and cognitive tasks and memory encoding.

We have discovered a class of novel compounds that potentiate the glutamate receptor. Compounds of the invention have been found to potentiate the glutamate receptor, and are expected to be useful in the treatment of disease states which require potentiation of such receptors, such as psychotic conditions, including schizophrenia. The compounds are also expected to be useful in the enhancement of cognition, for example in the treatment of cognition impairment brought about by various diseases.

According to a first aspect, the invention provides a compound of formula (I), or a salt, or solvate thereof

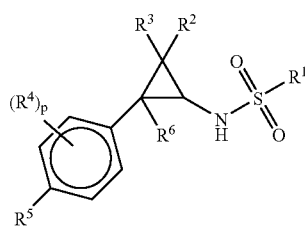

(I)

wherein
$R^1$ is selected from $C_{1-6}$alkyl, halo$C_{1-6}$alkyl, $C_{2-6}$alkenyl, amino, mono$C_{1-4}$alkylamino and di$C_{1-4}$alkylamino;
$R^2$, $R^3$ and $R^6$, which may be the same or different, are each independently selected from hydrogen, halogen, $C_{1-6}$alkyl, halo$C_{1-6}$alkyl and $C_{1-4}$alkoxy;
each $R^4$, which may be the same or different, is selected from $C_{1-6}$alkyl, halogen, halo$C_{1-6}$alkyl, $C_{1-4}$alkoxy, halo$C_{1-4}$alkoxy and cyano;
p is selected from 0, 1 and 2; and
$R^5$ is phenyl or an aromatic heterocyclyl, either of which is optionally substituted with one or more groups Y
each Y group is independently selected from the group consisting of: $C_{1-6}$alkyl, halogen, halo$C_{1-6}$alkyl, $C_{1-4}$alkoxy, halo$C_{1-4}$alkoxy, cyano, $—(CH_2)_qNR^{5a}SO_2R^{5b}$, $—(CH_2)_qNR^{5a}(C=O)R^{5d}$, $—(CH_2)_qNR^{5a}(C=O)N(R^{5c})_2$, $—(CH_2)_q(C=O)R^{5d}$, $—(CH_2)_qSO_2R^{5b}$; where $R^{5a}$ and each $R^{5c}$, which may be the same or different, is selected from hydrogen and $C_{1-6}$alkyl; $R^{5b}$ is selected from $C_{1-6}$alkyl and halo$C_{1-6}$alkyl; $R^{5d}$ is selected from $C_{1-6}$alkyl, $C_{1-4}$alkoxy and halo$C_{1-6}$alkyl; or $R^{5a}$ and $R^{5b}$, $R^{5a}$ and $R^{5c}$, or $R^{5a}$ and $R^{5d}$, where appropriate, together with the interconnecting atoms, may form a 5- or 6-membered ring; and q is 0, 1, or 2; in the case when there are two or more Y groups present, two of them together may form a cyclic group selected from $—(CH_2)_r, OR^{5e}O(CH_2)_s—$ and $—(CH_2)_rOR^{5e}—$ where $R^{5e}$ is a group selected from $C_{1-4}$alkylene or halo $C_{1-4}$alkylene; r and s are each independently 0, 1 or 2; and t is 2 or 3.

Unless otherwise indicated, any alkyl or alkylene group may be straight or branched and is of 1 to 6 carbon atoms, for example 1 to 4 or 1 to 3 carbon atoms.

Unless otherwise indicated, any alkenyl group may be straight or branched and is of 2 to 6 carbon atoms and may contain up to 3 double bonds which may be conjugated, for example vinyl, allyl and butadienyl.

Halo is selected from fluoro, chloro, bromo and iodo. For example, halo is selected from fluoro and chloro.

The term aromatic heterocyclyl as used herein describes a carbocyclic group, containing 1 to 4 heteroatoms independently selected from oxygen, nitrogen and sulphur and which contains at least one aromatic ring system. The aromatic heterocyclyl group may, for example, be monocyclic or bicyclic. It may also be tricyclic. A monocyclic aromatic heterocyclyl group may, for example, contain 5 to 7 ring atoms. A bicyclic aromatic heterocyclyl group may, for example, contain 7 to 12 ring atoms. In the case of bicyclic aromatic heterocyclyl groups, one ring or both rings may be aromatic. In the case of only one ring being aromatic, the one or more heteroatoms may be in the aromatic ring, in the non-aromatic ring or in both rings. A tricyclic aromatic heterocyclyl group may, for example, contain 10 to 14 ring atoms. In the case of tricyclic aromatic heterocyclyl groups, one, two or three rings may be aromatic. In the case of not all of the rings being aromatic, the one or more heteroatoms may be in an aromatic ring, or in a non-aromatic ring or in both types of rings.

Examples of monocyclic aromatic heterocyclyl groups are furyl, thienyl, pyrrolyl, imidazolyl, oxazolyl, thiazolyl, imidazolyl, pyrazolyl, isoxazolyl, isothiazolyl, oxadiazolyl, triazolyl, thiadiazolyl, pyridazinyl, pyridyl, pyrimidinyl, pyrazinyl, tetrazolyl, triazinyl, oxazepinyl, thiazepinyl, and diazepinyl.

In addition, the term heterocyclyl includes fused bicyclic heterocyclyl groups in which both rings are aromatic, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl, benzodioxanyl and isoindolyl.

Examples of bicyclic aromatic heterocyclyl groups in which only one ring is aromatic include phenyl fused with a diazabicycloalkane group, for example ethanoquinoxalinyl.

Examples of tricyclic aromatic heterocyclyl groups include carbazolyl, acridinyl, phenazinyl, phenothiazinyl, phenoxazinyl, thianthreninyl, anthraceninyl, acenaphthyleninyl, fluoreninyl and phenanthreninyl and the like.

In an embodiment the salt or solvate of the compound of formula (I) is a pharmaceutically acceptable salt or solvate. In one embodiment, the invention provides a compound of formula (I), a pharmaceutically acceptable salt, solvate or prodrug thereof.

In an embodiment $R^1$ is $C_{1-6}$ alkyl, for example $C_{1-4}$ alkyl. In a further embodiment $R^1$ is isopropyl or haloisopropyl, for example isopropyl.

In an embodiment $R^1$ is $C_{1-6}$ alkyl. In a further embodiment $R^1$ is isopropyl.

In an embodiment $R^2$, $R^3$ and $R^6$, which may be the same or different, are selected from hydrogen, halogen and $C_{1-6}$ alkyl. In a further embodiment $R^2$, $R^3$ and $R^6$, which may be the same or different, are selected from hydrogen, fluorine or methyl. In a still further embodiment $R^2$ and $R^3$ are hydrogen and $R^6$ is selected from hydrogen, fluorine and methyl.

In a still further embodiment $R^2$, $R^3$ and $R^6$ are hydrogen.

In an embodiment, when present, each $R^4$, which may be the same or different, is selected from $C_{1-6}$ alkyl and halogen. In a further embodiment, each $R^4$, which may be the same or different, is methyl or fluorine.

In an embodiment, p is 0.

In an embodiment, $R^5$ is selected from phenyl, pyridyl, pyrazinyl, pyrimidinyl, pyridazinyl, imidazolyl, pyrroyl, oxazolyl, thienyl, benzothiazolyl, benzofuranyl, benzimidazolyl and pyrazolyl. In a further embodiment, $R^5$ is selected from phenyl, pyridyl and pyrazinyl. In a further embodiment, $R^5$ is selected from phenyl, pyridyl, thienyl and benzthiazolyl. For example $R^5$ is selected from phenyl, pyridyl.

When $R^5$ is an aromatic heterocyclyl group, the heteroatom, or one of the, heteroatoms in the group $R^5$ may positioned ortho, meta or para to the point of attachment to the remainder of the molecule. For example, when $R^5$ is a pyridyl group, it may be positioned with the pyridyl nitrogen ortho, meta or para to the point of attachment to the remainder of the molecule.

In an embodiment, $R^5$ is phenyl, pyridyl, pyrazinyl, pyrimidinyl, pyridazinyl, imidazolyl, pyrroyl, oxazolyl or pyrazolyl, optionally substituted by one or more Y groups independently selected from those defined in the first aspect. In a further embodiment, $R^5$ is phenyl, pyridyl or pyrazinyl, optionally substituted by one or more Y groups independently selected from those defined in the first aspect.

In an embodiment, substituting group(s) Y which may be the same or different, are independently selected from $C_{1-6}$ alkyl, $C_{1-6}$ haloalkyl, $C_{1-6}$ alkoxy, $C_{1-6}$ haloalkoxy, cyano and halogen or two Y groups together form a cyclic group selected from —$(CH_2)_rOR^{5e}O(CH_2)_s$— and —$(CH_2)_tOR^{5e}$— where $R^{5e}$ is a group selected from $C_{1-4}$alkylene or halo $C_{1-4}$alkylene and where r and s are each independently 0, 1 or 2; and t is 2 or 3. In an embodiment, r and s are each be 0. In a further embodiment, R5e is selected from —$CH_2$— and —$CF_2$—. In one embodiment, the two Y groups forming such a cyclic group are on neighbouring atoms in the $R^5$ group.

In a further embodiment Y is selected from $C_{1-4}$ alkyl and halogen or two Y groups together form a group —O—$C_{1-4}$alkylene-O—. For example, Y is selected from methyl, fluoro and chloro or two Y groups together form a group —O—$CH_2$—O— or —O—$CF_2$—O—, for example methyl and fluoro. In one embodiment, Y is fluoro.

Each substituent Y may be positioned ortho, meta or para to the point of attachment of the group $R^5$ to the remainder of the molecule (or, where appropriate for non-six membered rings at any chemically available position). In one embodiment a substituent Y is positioned para or meta with respect to the point of attachment to the molecule of the main structure of the molecule.

In one embodiment, Y is selected from $C_{1-6}$alkyl, halogen, halo$C_{1-6}$alkyl, $C_{1-4}$alkoxy, halo$C_{1-4}$alkoxy, cyano, —$(CH_2)_q$NR$^{5a}$SO$_2$R$^{5b}$, —$(CH_2)_q$NR$^{5a}$(C=O)R$^{5d}$, —$(CH_2)_q$NR$^{5a}$(C=O)N(R$^{5c}$)$_2$, —$(CH_2)_q$(C=O)R$^{5d}$ and —$(CH_2)_q$SO$_2$R$^{5b}$; where $R^{5a}$ and each $R^{5c}$, which may be the same or different, is hydrogen or $C_{1-6}$alkyl; $R^{5b}$ is $C_{1-6}$alkyl or halo$C_{1-6}$alkyl; $R^{5d}$ is $C_{1-6}$alkyl, $C_{1-4}$alkoxy or halo$C_{1-6}$alkyl; or $R^{5a}$ and $R^{5b}$, $R^{5a}$ and $R^{5c}$, or $R^{5a}$ and $R^{5d}$, where appropriate, together with the interconnecting atoms, may form a 5- or 6-membered ring; and q is 0, 1, or 2.

In an embodiment, when $R^5$ is a substituted heterocyclyl, substituting groups Y which may be the same or different, are independently selected from $C_{1-6}$ alkyl and halogen.

In an embodiment, when $R^5$ is a substituted phenyl, substituting groups Y which may be the same or different, are independently selected from —$(CH_2)_q$NR$^{5a}$SO$_2$R$^{5b}$, —$(CH_2)_q$NR$^{5a}$(C=O)R$^{5d}$, —$(CH_2)_q$NR$^{5a}$(C=O)N(R$^{5c}$)$_2$, —$(CH_2)_q$(C=O)R$^{5d}$ and —$(CH_2)_q$SO$_2$R$^{5b}$; where $R^{5a}$ and each $R^{5c}$, which may be the same or different, is hydrogen or $C_{1-6}$alkyl; $R^{5b}$ is $C_{1-6}$alkyl or halo$C_{1-6}$alkyl; $R^{5d}$ is $C_{1-6}$alkyl, $C_{1-4}$alkoxy or halo$C_{1-6}$alkyl; or $R^{5a}$ and $R^{5b}$, $R^{5a}$ and $R^{5c}$, or $R^{5a}$ and $R^{5d}$, where appropriate, together with the interconnecting atoms, may form a 5- or 6-membered ring; and q is 0, 1, or 2.

Because of the presence of the cyclopropane ring, compounds of formula (I) possess at least two chiral centres, namely the attachment points of the sulphonamide and the phenyl ring on the cyclopropyl ring. The compounds may exist in four stereoisomers—a pair of diastereomers (cis and trans), each comprising a pair of enantiomers with respect to the chiral centres in the cyclopropane. It will also be appreciated, in common with most biologically active molecules that the level of biological activity may vary between the individual diastereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In an embodiment, the sulphonamide and phenyl substituents on the cyclopropyl ring are in a trans arrangement relative to each other.

Individual enantiomers of various of the example compounds have been prepared. As at the date of filing, it has not been possible to establish the absolute stereochemistry of the individual isomers. The individual isomers are identified by chiral HLPC retention times or by the chiral HPLC retention times of the intermediate starting materials from which they were prepared. Herein, a compound that has been prepared in racemic form has the suffix "racemic" and a compound that has been prepared in chiral form has the suffix "enantiomer 1" or "enantiomer 2". In one embodiment a compound of the invention in chiral form has at least 80% e.e. In another a compound of the invention in chiral form has at least 90% e.e., for example at least 95% e.e. In another embodiment the isomers correspond to at least 98% e.e, for example at least 99% e.e.

As mentioned above, in an embodiment, the sulphonamide and phenyl substituents on the cyclopropyl ring are in a trans arrangement relative to each other.

Accordingly, in an embodiment, the compound according to the first aspect is of formula (Ia) (whereby, for the avoidance of doubt, the directional indication of the bonds to the cyclopropyl ring indicates relative stereochemistry, not absolute stereochemistry):

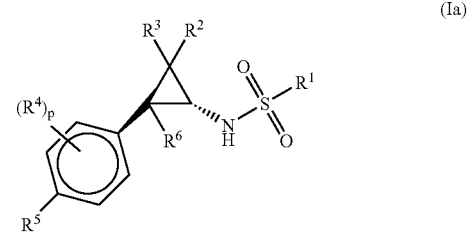

(Ia)

wherein $R^1$ to $R^5$ and p represent the groups as described above.

In an embodiment of the compound of formula (I) or (Ia), $R^1$ is $C_{1-6}$ alkyl;

$R^2$ and $R^3$ are hydrogen;

$R^6$ is hydrogen, halogen or methyl;

p is 0; and $R^5$ is pyridyl, pyrazinyl, pyrimidinyl, pyridazinyl, imidazolyl, pyrroyl, oxazolyl or pyrazolyl, optionally substituted by one or more groups Y independently selected from the group consisting of $C_{1-6}$ alkyl and halogen.

In an embodiment of the compound of formula (I) or (Ia), $R^1$ is $C_{1-6}$ alkyl;

$R^2$ and $R^3$ are hydrogen;

$R^6$ is hydrogen, halogen or methyl;

p is 0; and $R^5$ is pyridyl, optionally substituted by one or more groups Y independently, selected from the group consisting of $C_{1-6}$ alkyl and halogen.

In an embodiment of the compound of formula (I) or (Ia), $R^1$ is $C_{1-6}$ alkyl;

$R^2$ and $R^3$ are hydrogen;

$R^6$ is hydrogen, halogen or methyl;

p is 0; and $R^5$ is phenyl, optionally substituted by one or more groups independently, selected from the group consisting of selected from —$(CH_2)_q NR^{5a}SO_2R^{5b}$, —$(CH_2)_q NR^{5a}(C=O)R^{5d}$, —$(CH_2)_q NR^{5a}(C=O)N(R^{5c})_2$, —$(CH_2)_q(C=O)R^{5d}$ and —$(CH_2)_q SO_2R^{5b}$; where $R^{5a}$ and each $R^{5c}$, which may be the same or different, is hydrogen or $C_{1-6}$alkyl; $R^{5b}$ is $C_{1-6}$alkyl or halo$C_{1-6}$alkyl; $R^{5d}$ is $C_{1-6}$alkyl, $C_{1-4}$alkoxy or halo$C_{1-6}$alkyl; or $R^{5a}$ and $R^{5b}$, $R^{5a}$ and $R^{5c}$, or $R^{5a}$ and $R^{5d}$, where appropriate, together with the interconnecting atoms, may form a 5- or 6-membered ring; and q is 0, 1, or 2.

It will be appreciated that the present invention is intended to include compounds having any combination of the groups listed hereinbefore.

It will be understood that, where appropriate, an embodiment described above for one part of the invention may be combined with an embodiment of another part of the invention.

Examples of compounds of formula (I) include:

Trans-N-{-2-[4-(6-fluoro-3-pyridinyl)phenyl]cyclopropyl}-2-propanesulfonamide racemic (Example 1).

In one embodiment, the invention provides Trans-N-{-2-[4-(6-fluoro-3-pyridinyl)phenyl]cyclopropyl}-2-propanesulfonamide racemic (Example 1) and salts and solvates thereof.

Further examples of compounds of formula (I) include:

Trans-N-{-2-[4-(6-methyl-3-pyridinyl)phenyl]cyclopropyl}-2-propanesulfonamide racemic (Example 2);

Trans-N-{-2-[4-(5-fluoro-2-pyridinyl)phenyl]cyclopropyl}-2-propanesulfonamide racemic (Example 3);

Trans-N-{-2-[4-(5-chloro-2-pyridinyl)phenyl]cyclopropyl}-2-propanesulfonamide racemic (Example 4)

Trans-N-{-2-[4-(5-fluoro-phenyl)phenyl]cyclopropyl}-2-propanesulfonamide racemic (Example 5)

Trans-N-{-2-[4-(4-cyano-phenyl)phenyl]cyclopropyl}-2-propanesulfonamide racemic (Example 6)

Trans-N-{(2-[4-(1,3-benzodioxol-5-yl)phenyl]cyclopropyl}-2-propanesulfonamide racemic (Example 7)

Trans-N-{-2-[3-(thienyl)phenyl]cyclopropyl}-2-propanesulfonamide racemic (Example 8)

Trans-N-{-2-[2-(thienyl)phenyl]cyclopropyl}-2-propanesulfonamide racemic (Example 9)

Trans-N-{-2-[4-(5-fluoro-3-pyridinyl)phenyl]cyclopropyl}-2-propanesulfonamide racemic (Example 10)

Trans-N-{-2-[4-(5-methyl-3-pyridinyl)phenyl]cyclopropyl}-2-propanesulfonamide racemic (Example 11)

Trans-N-{2-[4-(5-fluoro-3-pyridinyl)phenyl]cyclopropyl}-2-propanesulfonamide enantiomer 1 (Example 12 Enantiomer 1)

Trans-N-{2-[4-(5-fluoro-3-pyridinyl)phenyl]cyclopropyl}-2-propanesulfonamide enantiomer 2 (Example 12 Enantiomer 2)

Trans-N-{2-[4-(6-fluoro-3-pyridinyl)phenyl]cyclopropyl}-2-propanesulfonamide Enantiomer 1 (Example 13 Enantiomer 1)

Trans-N-{2-[4-(6-fluoro-3-pyridinyl)phenyl]cyclopropyl}-2-propanesulfonamide Enantiomer 2 (Example 13 Enantiomer 2)

Trans-N-{2-[4-(5-fluoro-2-pyridinyl)phenyl]cyclopropyl}-2-propanesulfonamide Enantiomer 1 (Example 14 Enantiomer 1)

Trans-N-{2-[4-(5-fluoro-2-pyridinyl)phenyl]cyclopropyl}-2-propanesulfonamide Enantiomer 2 (Example 14 Enantiomer 2)

Trans-N-{2-[4-(5-chloro-2-pyridinyl)phenyl]cyclopropyl}-2-propanesulfonamide Enantiomer 1 (Example 15 Enantiomer 1)

Trans-N-{2-[4-(5-chloro-2-pyridinyl)phenyl]cyclopropyl}-2-propanesulfonamide Enantiomer 2 (Example 15 Enantiomer 2)

Trans-N-[2-(4'-fluoro-4-biphenylyl)cyclopropyl]-2-propanesulfonamide Enantiomer 1 (Example 16 Enantiomer 1)

Trans-N-[2-(4'-fluoro-4-biphenylyl)cyclopropyl]-2-propanesulfonamide Enantiomer 2 (Example 16 Enantiomer 2)

Trans-N-[2-(4'-cyano-4-biphenylyl)cyclopropyl]-2-propanesulfonamide Enantiomer 1 (Example 17 Enantiomer 1)

Trans-N-{2-[4-(1,3-benzodioxol-5-yl)phenyl]cyclopropyl}-2-propanesulfonamide Enantiomer 2 (Example 18 Enantiomer 2)

Trans-N-{2-[4-(5-methyl-3-pyridinyl)phenyl]cyclopropyl}-2-propanesulfonamide Enantiomer 1 (Example 19 Enantiomer 1)

Trans-N-{2-[4-(5-methyl-3-pyridinyl)phenyl]cyclopropyl}-2-propanesulfonamide Enantiomer 2 (Example 19 Enantiomer 2)

Trans-N-{2-[4-(2,2-difluoro-1,3-benzodioxol-5-yl)phenyl]cyclopropyl}-2-propanesulfonamide Enantiomer 2 (Example 20 Enantiomer 2)

Trans-N-{2-[3'-(methyloxy)-4-biphenylyl]cyclopropyl}-2-propanesulfonamide Enantiomer 2 (Example 21 Enantiomer 1)

Trans-N-{2-[4-(2-pyridinyl)phenyl]cyclopropyl}-2-propanesulfonamide Enantiomer 1 (Example 22 Enantiomer 1)

Trans-N-{2-[4-(2-pyridinyl)phenyl]cyclopropyl}-2-propanesulfonamide Enantiomer 2 (Example 22 Enantiomer 2)

Trans-N-(2-{4-[6-(methyloxy)-3-pyridinyl]phenyl}cyclopropyl)-2-propanesulfonamide Enantiomer 2 (Example 23 Enantiomer 2)

Trans-N-(2-{4-[3-(methyloxy)-2-pyridinyl]
phenyl}cyclopropyl)-2-propanesulfonamide Enantiomer
1 (Example 24 Enantiomer 1)
Trans-N-(2-{4-[3-(methyloxy)-2-pyridinyl]
phenyl}cyclopropyl)-2-propanesulfonamide Enantiomer
2 (Example 24 Enantiomer 2)
Trans-N-{2-[4-(2-methyl-1,3-benzothiazol-5-yl)phenyl]cy-
clopropyl}-2-propanesulfonamide Enantiomer 2 (Ex-
ample 25 Enantiomer 2);

and salts and solvates thereof.

For the avoidance of doubt, unless otherwise indicated, the term substituted means substituted by one or more defined groups. In the case where groups may be selected from a number of alternative groups, the selected groups may be the same or different.

For the avoidance of doubt, the term independently means that where more than one substituent is selected from a number of possible substituents, those substituents may be the same or different.

In one embodiment, an appropriate compound of formula (I) may be in the form of a salt. For example, such a salt may be a pharmaceutically acceptable salt. Suitable pharmaceutically acceptable salts of the compounds of formula (I) include acid salts, for example sodium, potassium, calcium, magnesium and tetraalkylammonium and the like, or mono- or dibasic salts with the appropriate acid for example organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids and the like. Other salt forms that are not pharmaceutically acceptable, for example a salt that is useful as an intermediate, also form part of the present invention.

Furthermore, some of the crystalline forms of the compounds of structure (I) may exist as polymorphs, which are included in the present invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of solvent (including water) where non-stoichiometric solvates (hydrates in the case of water) may be produced by processes such as lyophilisation).

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may be administered as pro-drugs. Examples of pro-drug forms for certain compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Examples of prodrugs for certain compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Hereinafter, compounds of formula (I), their salts and their solvates defined in any aspect of the invention (except Intermediate compounds in chemical processes) are referred to as "compounds of the invention".

The compounds of the invention may exist in one or more tautomeric forms. All tautomers and mixtures thereof are included in the scope of the present invention.

Compounds of the invention may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods (for example chiral HPLC), or any given isomer may be obtained by conventional synthetic methods or by stereospecific or asymmetric syntheses.

Since the compounds of the invention are intended for use in pharmaceutical compositions it will readily be understood that they are each optionally provided in substantially pure form, for example at least 60% pure, for example at least 75% pure or at least 85%, or at least 98% pure (% are on a weight for weight basis). Impure preparations of the compounds may be used for preparing the more pure forms used in the pharmaceutical compositions; these less pure preparations of the compounds should contain at least 1%, or at least 5% or from 10 to 59% of a compound of the invention.

Compounds of the invention may be prepared in a variety of ways. In the following reaction schemes and hereafter, unless otherwise stated $R^1$ to $R^6$, p and q are as defined in the first aspect. These processes form further aspects of the invention.

Throughout the specification, general formulae are designated by Roman numerals (I), (II), (III), (IV) etc. Subsets of these general formulae are defined as (Ia), (Ib), (Ic) etc. . . . (IVa), (IVb), (IVc) etc.

A compound of formula (I) may be prepared by coupling a compound of formula (II) where X is a leaving group such as halogen (for example chlorine, bromine or iodine) with a boronic acid derivative of formula (III) according to reaction scheme 1. Typical coupling conditions comprise heating a compound of formula (II), a compound of formula (III), a base (or potassium fluoride where the leaving group is chlorine), 2-(di-tert-butylphosphino)biphenyl and palladium(II) acetate in dry tetrahydrofuran at about 140 degC. The method of Scheme 1 is particularly suitable for compounds of the invention in which $R^5$ is aromatic heterocyclyl, for example pyridyl.

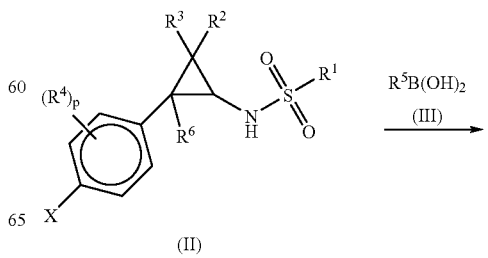

Scheme 1

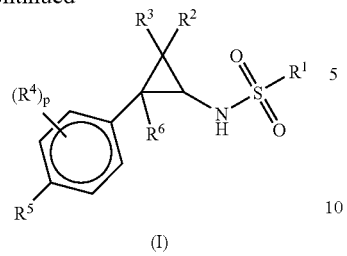

(I)

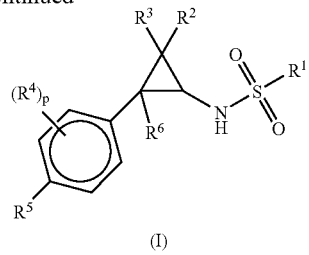

(I)

Alternatively, a compound of formula (I) may be prepared by treating a boronate compound of formula (IIa) with a compound $R^5$—X (IIIa) where X is a leaving group such as halogen (for example bromine or iodine) as shown in Scheme 1b. For example the boronate may be a 4,4,5,5-tetramethyl-1,3,2-dioxaborolan-2-yl compound as shown in Scheme 1b. Typical reaction conditions comprise heating the boronate compound (IIa) with a compound of formula (IIIa), a base (or potassium fluoride where the leaving group is chlorine) and a suitable catalyst (for example a palladium catalyst, such as palladium(II)acetate of palladium tetrakis, which may be polymer-supported) in a suitable solvent (for example dry 1,4-dioxane) at for example, about 90° C. Suitable bases include sodium carbonate solution The boronate compound (IIa) may be prepared by reaction of a compound of formula (II) with a suitable diboron compound. Typical coupling conditions comprise heating the compound of formula (II) (for example at approximately 90° C.) with the diboron compound (for example bis(pinacolato) diboron) in a suitable solvent (for example dioxane) in the presence of a suitable base (for example potassium acetate) to produce a compound of formula (IIa).

The method of Scheme 2 is particularly suitable for compounds of the invention in which $R^5$ is phenyl or aromatic heterocyclyl, for example phenyl, pyridyl, thienyl or benzthiazolyl Accordingly the invention provides a method of preparing a compound of the invention comprising a) coupling a compound of formula (II) where X is a leaving group such as halogen (for example chlorine, bromine or iodine) with a boronic acid derivative of formula (III)

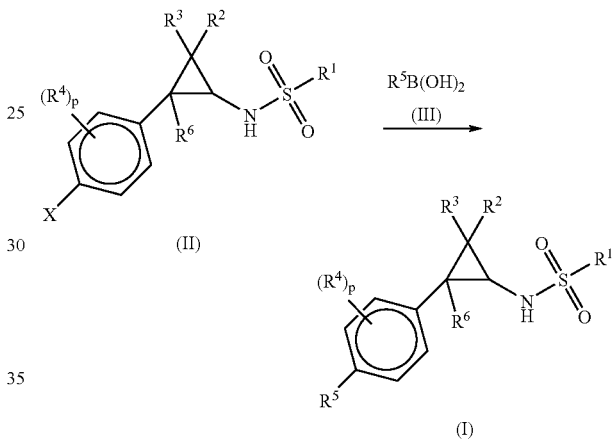

or b) coupling a boronate compound of formula (IIa) with a compound $R^5$—X (IIIa) where X is a leaving group such as halogen (for example bromine or iodine)

Scheme 1b

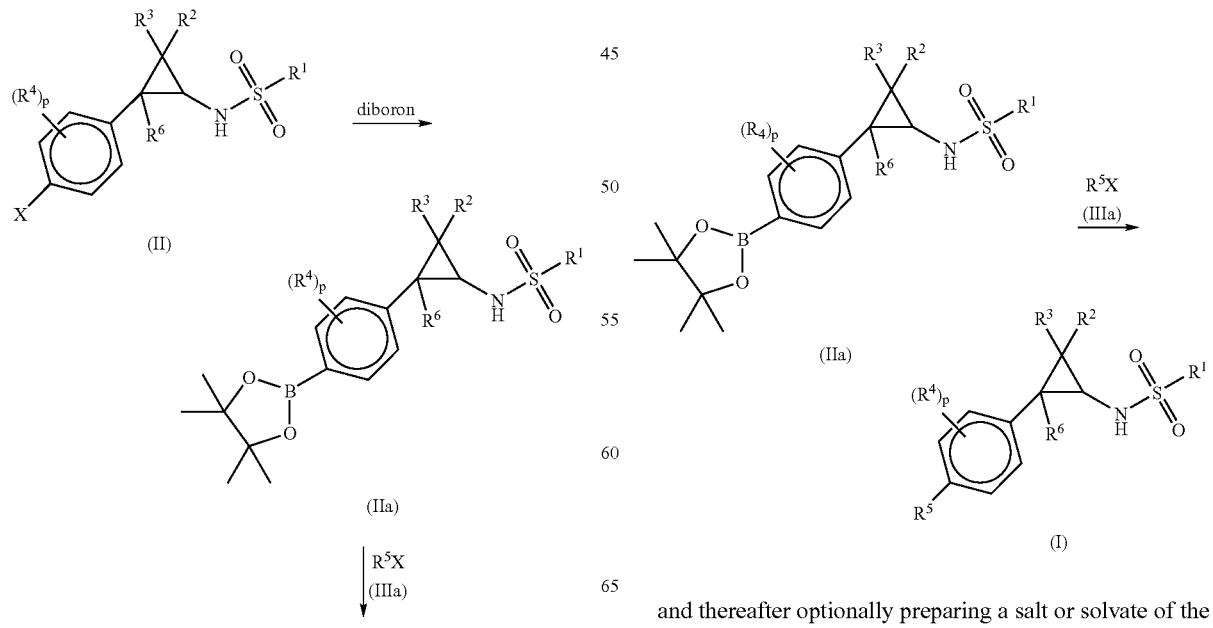

and thereafter optionally preparing a salt or solvate of the product.

Compounds of formula (II) may be prepared from compounds of formula (IV) according to reaction scheme 2. Typical reaction conditions are adding a sulfonyl chloride (V) to an ice-cooled mixture of (IV) and a base (such as diisopropylamine) in a suitable solvent (such as dichloromethane) and then warming the mixture gradually to room temperature.

Scheme 2

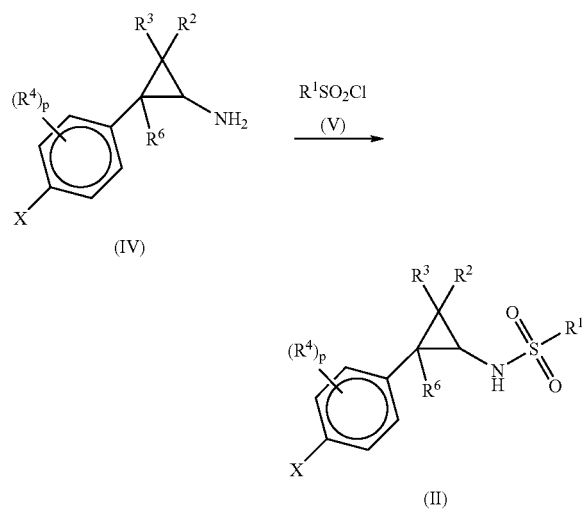

Compounds of formula (IV) may be prepared using procedures available to the person skilled in the art (see Bioorganic and Medical Chemistry 12(9), 2021-2034, 2004) or adaptations thereof.

For example, fluorinated compounds of formula (IVa) can be prepared from compounds of formula (VI) according to reaction scheme 3. Standard procedures, well known to the person skilled in the art can be used to carry out this reaction.

Scheme 3

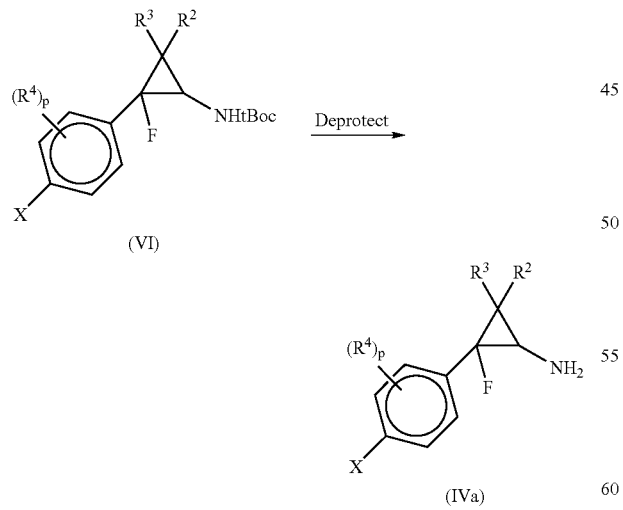

Compounds of formula (VI) in which X=Cl are known (Journal of Fluorine Chemistry 114(2), 189-198, 2002 and Synthesis (10) 1479-1490, 2000).

For example, the cyclopentyl group may be introduced into the molecule means of reaction of a suitable styrene with ethyl diazoacetate. The invention thus provides a method for preparing compounds of the invention wherein intermediate (II) or (IIa) has been prepared by a method comprising the step of adding ethyl diazoacetate to a suitable styrene (X) where X is a group such as halogen (for example chlorine, bromine or iodine), optionally in the presence of a suitable catalyst followed by elaborating the product (XI) to a compound of formula (II) or (IIa).

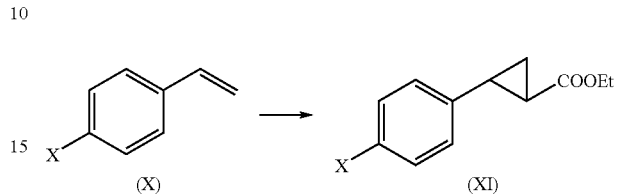

It may be desirable to prepare compounds of the invention in diastereomerically- and/or enantiomerically-pure form. Such preparation may be carried out by a non-stereospecific synthesis followed by separation of the diastereoisomer or enantiomer products. Alternatively, it may be carried out by a stereoselective synthesis. For example, intermediate compound (IV) may be prepared in a stereoselective fashion. A suitable scheme for such a synthesis is shown in Scheme 4.

Scheme 4

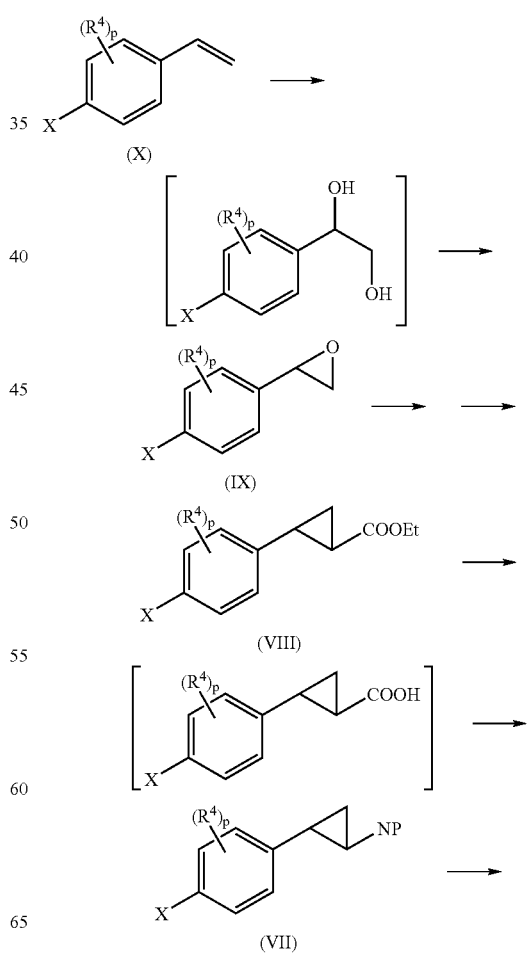

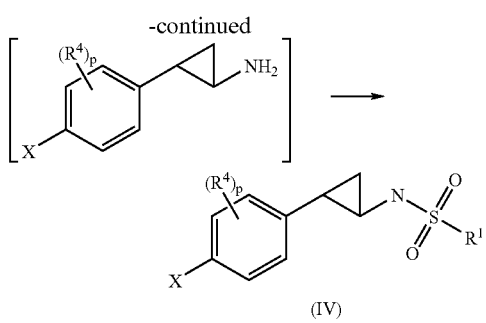

(IV)

Starting from a suitable styrene (X), a stereoselective epoxidation may be carried out using a suitable catalyst. For example AD-mix-β or AD-mix-α may be used. Such a reaction is typically carried out in water and an alcohol (for example $^t$butanol) at reduced temperature (for example 0° C.) followed by addition of a suitable reducing agent (for example sodium sulfite).

Compound (IX) is then elaborated to ester compound (VIII) by reaction with a suitable base (for example sodium t-butoxide) and suitable reagent (for example triethyl phosphonoacetate) in a suitable solvent (for example DME) at approximately room temperature. In turn, ester compound (VIII) is elaborated to a corresponding protected amine (VII) (for example the Boc-protected amide) by conventional group interconversion. The deprotected amine is then converted to the sulphonamide as set out in Scheme 2.

Accordingly, the invention provides a method of preparing compounds of the invention in chiral form comprising the step of stereoselectively epoxidising a suitable styrene (X) where X is a leaving group such as halogen (for example chlorine, bromine or iodine), followed by elaborating the product of the epoxidation to a compound of the invention.

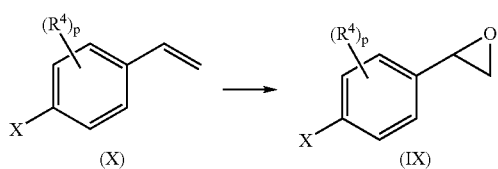

Further details for the preparation of compounds of formula (I) are found in the Examples section hereinafter.

The compounds of the invention may be prepared singly or as compound libraries comprising at least 2, for example 5 to 1,000 compounds, for example 10 to 100 compounds. Libraries of compounds of the invention may be prepared by a combinatorial 'split and mix' approach or by multiple parallel synthesis using either solution phase or solid phase chemistry, by procedures known to those skilled in the art. Thus according to a further aspect there is provided a compound library comprising at least 2 compounds of the invention.

Compounds of the invention may be administered in combination with other therapeutic agents, for example an antipsychotic (such as olanzapine, risperidone, clozapine, ziprazidone and talnetant).

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, for example water. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration.

The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit may, for example contain from 0.1 to 20 mg of the active ingredient. For example, such a unit may contain from 1 to 10 mg. The dosage as employed for adult human treatment may, for example, range from 2 to 50 mg per day, for instance 5 to 20 mg per day depending on the route and frequency of administration (though in some instances, a dosage of 50 mg to 100 mg per day may be appropriate). Based on a 75 kg individual, such a dosage corresponds to 0.027 to 0.667 mg/kg per day. Suitably the dosage is from 0.05 to 0.3 mg/kg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e. the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The embodiments described in respect of the first aspect apply equally to each of these further aspects:

i) a pharmaceutical composition comprising a compound of the invention and at least one pharmaceutically acceptable carrier or diluent;

ii) the use of a compound of the invention in the manufacture of a medicament for treating or preventing a disease or condition caused by a reduction or imbalance in glutamate receptor function in a mammal;

iii) a compound of the invention for use in treating or preventing a disease or condition caused by a reduction or imbalance in glutamate receptor function in a mammal;

iv) a compound of the invention for use as a medicament; and v) a method of treatment or prevention of a disease or condition caused by a reduction or imbalance in glutamate receptor function in a mammal comprising administering an effective amount of a compound of the invention.

Furthermore, the invention also provides a combination product of a compound of the invention with an antipsychotic. In addition, the invention provides:

i) a pharmaceutical composition comprising such a combination product and at least one pharmaceutically acceptable carrier or diluent;

ii) the use of such a combination in the manufacture of a medicament for treating or preventing a disease or condition caused by a reduction or imbalance in glutamate receptor function in a mammal;

iii) such a combination product for use in treating or preventing a disease or condition caused by a reduction or imbalance in glutamate receptor function in a mammal;

iv) such a combination product for use as a medicament;

v) a method of treatment or prevention of a disease or condition caused by a reduction or imbalance in glutamate receptor function in a mammal comprising administering an effective amount of such a combination product.

In the case of aspects ii), iii) and v), relevant diseases or conditions are: psychosis and psychotic disorders (including schizophrenia, schizo-affective disorder, schizophreniform diseases, brief reactive psychosis, child onset schizophrenia, "schizophrenia-spectrum" disorders such as schizoid or schizotypal personality disorders, acute psychosis, alcohol psychosis, drug-induced psychosis, autism, delerium, mania (including acute mania), manic depressive psychosis, hallucination, endogenous psychosis, organic psychosyndrome, paranoid and delusional disorders, puerperal psychosis, and psychosis associated with neurodegenerative diseases such as Alzheimer's disease); cognitive impairment (e.g. the treatment of impairment of cognitive functions including attention, orientation, memory (i.e. memory disorders, amnesia, amnesic disorders and age-associated memory impairment) and language function, and including cognitive impairment as a result of stroke, Alzheimer's disease, Aids-related dementia or other dementia states, as well as other acute or sub-acute conditions that may cause cognitive decline such as delirium or depression (pseudodementia states) trauma, aging, stroke, neurodegeneration, drug-induced states, neurotoxic agents), mild cognitive impairment, age related cognitive impairment, autism related cognitive impairment, Down's syndrome, cognitive deficit related to psychosis, post-electroconvulsive treatment related cognitive disorders; anxiety disorders (including generalised anxiety disorder, social anxiety disorder, agitation, tension, social or emotional withdrawal in psychotic patients, panic disorder, and obsessive compulsive disorder); neurodegenerative diseases (such as Alzheimer's disease, amyotrophic lateral sclerosis, motor neurone disease and other motor disorders such as Parkinson's disease (including relief from locomotor deficits and/or motor disability, including slowly increasing disability in purposeful movement, tremors, bradykinesia, hyperkinesia (moderate and severe), akinesia, rigidity, disturbance of balance and co-ordination, and a disturbance of posture), dementia in Parkinson's disease, dementia in Huntington's disease, neuroleptic-induced Parkinsonism and tardive dyskinesias, neurodegeneration following stroke, cardiac arrest, pulmonary bypass, traumatic brain injury, spinal cord injury or the like, and demyelinating diseases such as multiple sclerosis and amyotrophic lateral sclerosis); depression (which term includes bipolar (manic) depression (including type I and type II), unipolar depression, single or recurrent major depressive episodes with or without psychotic features, catatonic features, melancholic features, atypical features (e.g. lethargy, over-eating/obesity, hypersomnia) or postpartum onset, seasonal affective disorder and dysthymia, depression-related anxiety, psychotic depression, and depressive disorders resulting from a general medical condition including, but not limited to, myocardial infarction, diabetes, miscarriage or abortion); post-traumatic stress syndrome; attention deficit disorder; attention deficit hyperactivity disorder; drug-induced (phencyclidine, ketamine and other dissociative anaesthetics, amphetamine and other psychostimulants and cocaine) disorders; Huntingdon's chorea; tardive dyskinesia; dystonia; myoclonus; spasticity; obesity; stroke; sexual dysfunction; and sleep disorders. Relevant diseases also include some forms of epilepsy.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Compounds of the invention may also be of use in the treatment of the following disorders:—

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9):

Enhancement of cognition including the treatment of cognition impairment in other diseases such as schizophrenia, bipolar disorder, depression, other psychiatric disorders and psychotic conditions associated with cognitive impairment, e.g. Alzheimer's disease: and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

All of the various forms and sub-forms of the disorders mentioned herein are contemplated as part of the present invention.

Within the context of the present invention, the term "cognitive impairment" includes for example the treatment of impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

The compounds of the invention may be used in combination with the following agents to treat or prevent psychotic disorders: i) antipsychotics (such as olanzapine, risperidone, clozapine, ziprazidone and talnetant); ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example lofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstrual agents for example pyridoxine and progesterones.

The compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstrual agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent Attention Deficit Hyperactivity Disorder: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone, amisulpride, ziprazidone and talnetant).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

EXAMPLES

The invention is illustrated by the Examples described below.

Starting materials were obtained from commercial suppliers and used without further purification unless otherwise stated. Flash chromatography was carried out using prepacked Isolute Flash™ or Biotage™ silica-gel columns as the stationary phase and analytical grade solvents as the eluent.

NMR spectra were obtained at 298K, at the frequency stated using either a Bruker™ DPX400 or an Oxford Instruments™ 250 MHz machine and run as a dilute solution of $CDCl_3$ unless otherwise stated. All NMR spectra were reference to tetramethylsilane (TMS $\delta_H$ 0, $\delta_C$ 0). All coupling constants are reported in hertz (Hz), and multiplicities are labelled s (singlet), bs, (broad singlet), d (doublet), t (triplet), q (quartet), dd (doublet of doublets), dt (doublet of triplets) and m (multiplet).

Total ion current traces were obtained for electrospray positive and negative ionisation (ES+/ES−) and atmospheric pressure chemical positive and negative ionisation (AP+/AP−).

Preparative Chromatography

Preparative chromatography was carried out using either an XTerrra C18 5 µm column (100×19 mm) or a GEMINI C18 5 µm (100×21 mm) column. The mobile phase was mixture of 10 mM $NH_4HCO_3$ pH10 (A) and $CH_3CN$ (B). A gradient was applied starting with a 30% (B) solution and increasing the amount of (B) from 30% to 95% over 12 mins at a flow rate of 17 ml/min. Ionisation mode was generally ES+ but ES− for example 6.

ABBREVIATIONS

| Abbreviations | |
|---|---|
| DCM | Dichloromethane |
| TEA | Triethylamine |
| TMS-Cl- | Trimethylsilyl chloride |
| DME | Dimethoxy ether |
| ss | saturated solution |
| TFA | Trifluoroacetic acid |
| DAD | Diode Array Detector |
| CD | Circular dichroism |
| a/a % | percentage by area unde the curve |

In the procedures that follow, reference to an Intermediate or Example by number is typically provided. This is provided merely for assistance to the skilled chemist to identify the starting material used. The starting material may not necessarily have been prepared from the batch referred to.

9.225 mmol) was added, followed by the dropwise addition of isopropylsulfonyl chloride (877 mg, 6.15 mmol) with stirring under an atmosphere of argon. The reaction mixture was allowed to warm to room temperature and stirred for 1 h. The reaction mixture was then washed with 1 N HCl (2×50 ml). The organic layer was dried over sodium sulphate and evaporated in vacuo to give a yellow oil. The crude product was chromatographed on a 5 g isolute silica Sep-Pak® column eluting from 0-50% ethyl acetate in petroleum ether to give the title compound (570 mg, 68%); mass spectrum (API−): Found 272 (MH−);

$C_{12}H_{16}{}^{35}ClNO_2S$ requires 273; $^1$H-NMR (400 MHz, CDCl$_3$): 1.33 (2H, m), 1.40 (6H, m), 2.42 (1H, m), 2.67 (1H, m), 3.25 (1H, m), 4.68 (1H, bs), 7.04 (2H, m), 7.24 (2H, m).

Preparation of Trans-N-[2-(4-bromophenyl)cyclopropyl]-2-propanesulfonamide Racemic and Corresponding Chiral Material Enantiomer 1 and Enantiomer 2

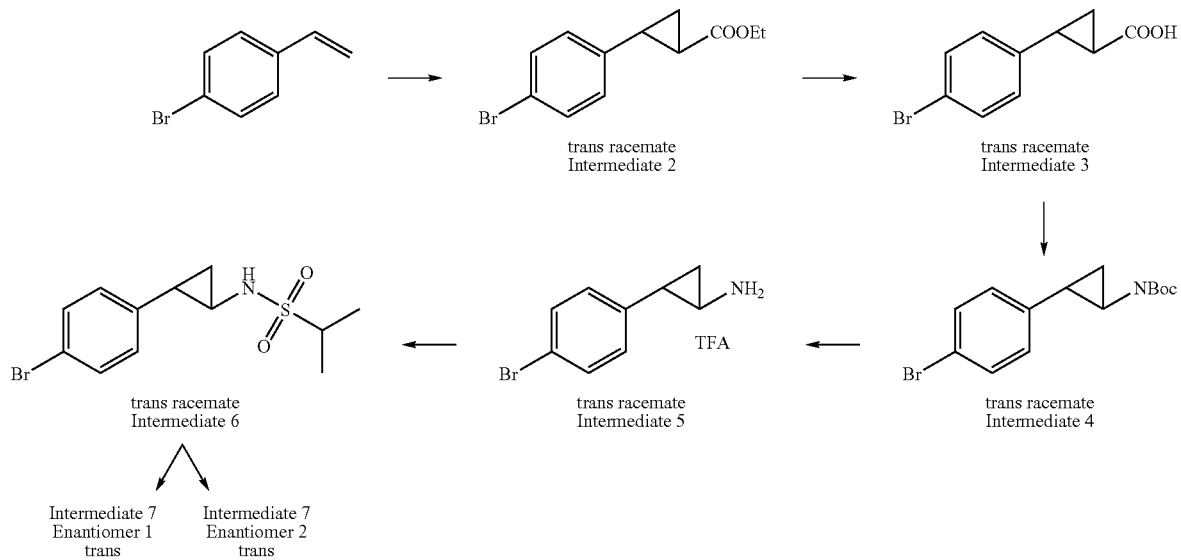

Intermediates

Intermediate 1: Trans-N-[(-2-(4-chlorophenyl)cyclopropyl]-2-propanesulfonamide racemic

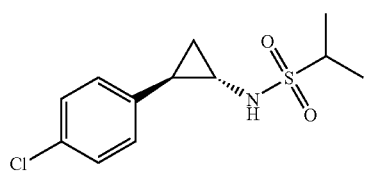

Trans-2-(4-chlorophenyl)cyclopropanamine hydrochloride (see Bioorganic and Medical Chemistry 12(9), 2021-2034, 2004) (628 mg, 3.08 mmol) was suspended in dry dichloromethane (15 ml) and cooled to 0° C. with stirring under argon. 1,8-Diazabicyclo[5.4.0]undec-7-ene (1.40 g,

Intermediate 2: Trans-ethyl 2-(4-bromophenyl)cyclopropanecarboxylate racemic 4-Br-styrene (10 g, 54.62 mmol) and Rh$_2$(AcOEt)$_4$ (241.3 mg, 0.546 mmol) were dissolved in 45 ml of dry DCM. To the solution was added of a solution of ethyl diazoacetate (5.74 mL, 54.62 mmol) in 60 ml DCM dropwise over 1.5 h. After 4 h, a further solution of 1 mL ethyl diazoacetate in 10 mL dry DCM was added drop wise. The obtained solution was stirred at room temperature overnight. Then the solvent was removed in vacuo to obtain approximately 18 g of crude title material that was purified by SiO$_2$ flash chromatography (Horizon 65M) in two 9 g portions, eluting with hexane/Et$_2$O from 98/2 to 96/4. Evaporation of the solvent afforded 5.15 g of pure title material as a white solid.

NMR (CDCl$_3$): 7.40 (d, 2H), 6.98 (d, 2H), 4.18 (q, 2H), 2.48 (m, 1H), 1.87 (m, 1H), 1.61 (M, 1H), 1.29 (t, 3H), 1.28 (m, 1H).

Intermediate 3: Trans-2-(4-bromophenyl)cyclopropanecarboxylic acid racemic

To a solution of racemic trans-ethyl 2-(4-bromophenyl) cyclopropanecarboxylate (Intermediate 2) (4.97 g, 18.47 mmol) in 76.72 mL of EtOH was added dropwise 49.08 mL of 2N NaOH and the mixture was stirred at room temperature for 1 h. The solution was then concentrated in vacuo, 20 mL of water were added and the aqueous phase washed with 2×20 mL Et$_2$O. The aqueous phase was then acidified with 2M HCl to pH 3 (approx.) and extracted with 3×100 mL Et$_2$O. The collected organic phases were dried over Na$_2$SO$_4$, filtered and concentrated in vacuo to get 4.43 g of the title compound as a white solid, which was used in the next step without further purification.

NMR (d$_6$-DMSO): 12.36 (bs, 1H), 7.44 (d, 2H), 7.13 (d, 2H), 2.38 (m, 1H), 1.80 (m, 1H), 1.42 (m, 1H), 1.32 (m, 1H).

Intermediate 4: Trans-1,1-dimethylethyl [2-(4-bromophenyl)cyclopropyl]carbamate racemic To a solution of racemic trans-1,1-dimethylethyl [2-(4-bromophenyl)cyclopropyl]carbamate (Intermediate 3) (4.32 g, 17.92 mmol) in 55.4 mL of dry $^t$BuOH was added TEA (3.5 mL, 24.73 mmol) and diphenylphosphoryl azide (4.24 mL, 19.71 mmol). The mixture was stirred at 90° C. under nitrogen overnight then concentrated in vacuo and poured into 10% aqueous Na$_2$CO$_3$. The aqueous phase was extracted with 3×300 mL Et$_2$O and the collected organics dried over Na$_2$SO$_4$ and concentrated in vacuo to get crude material (8.65 g) that was purified by SiO$_2$ flash chromatography (Horizon 65M) eluting with cyclohexane/ethyl acetate from 90/10 to 80/20. Evaporation of the solvent in vacuo afforded 2.1 g of pure title material as an off white solid.

NMR (CDCl$_3$): 7.38 (d, 2H), 7.03 (d, 2H), 4.82 (bs, 1H), 2.68 (m, 1H), 2.02 (m, 1H), 1.46 (s, 9H), 1.14 (m, 2H).

Intermediate 5: Trans-[2-(4-bromophenyl)cyclopropyl]amine trifluoroacetic acid salt racemic A solution of racemic trans-1,1-dimethylethyl [2-(4-bromophenyl)cyclopropyl]carbamate (Intermediate 4) (1.25 g) in 71.5 mL of DCM was cooled to 0° C. TFA (17 mL) was added dropwise and the solution was stirred at this temperature for 1 h. Then the mixture was evaporated in vacuo to obtain 1.83 g of title material as a yellow solid which was used without further purification in the next step.

Intermediate 6: Trans-N-[2-(4-bromophenyl)cyclopropyl]-2-propanesulfonamide racemic Racemic trans-[2-(4-bromophenyl)cyclopropyl]amine trifluoroacetic acid salt (Intermediate 5) (1.814 g, 5.563 mmol) was suspended in 40 mL dry DCM and the mixture was cooled to −15° C. To the solution was added dropwise TEA (2.326 mL, 16.689 mmol) followed by isopropyl sulphonyl chloride (0.625 mL, 5.563 mmol). The mixture was stirred at this temperature for 1 h and then further TEA (0.62 mL) followed by further isopropyl sulphonyl chloride (0.25 mL) were added dropwise into the solution. After further 0.5 h stirring at this temperature, the solution was taken up with 100 mL of DCM and washed with 50 mL of water. The aqueous phase was extracted with 100 mL DCM and the collected organic phases washed twice with water, dried over Na$_2$SO$_4$ and concentrated in vacuo to obtain crude material (1.413 g) that was purified by SiO$_2$ flash chromatography (Horizon 40M) eluting with cyclohexane/ethyl acetate from 80/20 to 70/30. Evaporation of the solvent in vacuo afforded 0.976 g of pure title material.

NMR (CDCl$_3$): 7.40 (d, 2H), 7.00 (d, 2H), 4.62 (s, 1H), 3.26 (m, 1H), 2.69 (m, 1H), 2.25 (m, 1H), 1.42 (d, 3H), 1.40 (d, 3H), 1.34 (m, 1H), 1.22 (m, 1H).

Intermediate 6 was prepared several times on a similar scale with similar yields and the products were combined.

Intermediate 7 Enantiomer 1: Trans-N-[2-(4-bromophenyl)cyclopropyl]-2-propanesulfonamide, Enantiomer 1

Intermediate 7 Enantiomer 2: Trans-N-[2-(4-bromophenyl)cyclopropyl]-2-propanesulfonamide Enantiomer 2

0.35 g of racemic trans-N-[2-(4-bromophenyl)cyclopropyl]-2-propanesulfonamide (Intermediate 6) was separated by preparative chiral HPLC into Intermediate 7 Enantiomer 1 and Intermediate 7 Enantiomer 2, according to the chiral HPLC elution order.

Evaporation of the Solvent Afforded:
  Intermediate 7, Enantiomer 1,155 mg as a white solid
  Chiral HPLC: ee=99.68%
  Intermediate 7, Enantiomer 2, 155 mg as a white solid
  Chiral HPLC: ee >99.99%

Analytical Chiral HPLC Conditions:
  column: CHIRALPAK AS-H (25×0.46 cm)
  mobile phase: n-Hexane/Ethanol 87/13% v/v
  flow rate: 1 ml/min
  DAD: 225 nm
  CD: 255 nm
  Rt Enantiomer 1: 10.51 min
  Rt Enantiomer 2: 11.58 min Preparative Chiral HPLC Conditions:
  Column: Chiralpak AS-H (25×2 cm)
  mobile phase: n-Hexane/Ethanol 87/13% v/v
  Flow rate: 15 ml/min
  UV at 225 nm
  Rt Enantiomer 1: 12.95 min
  Rt Enantiomer 2: 14.07 min

Intermediate 8: Trans-N-{2-[4-(4,4,5,5-tetramethyl-1,3,2-dioxaborolan-2-yl)phenyl]cyclopropyl}-2-propanesulfonamide racemic

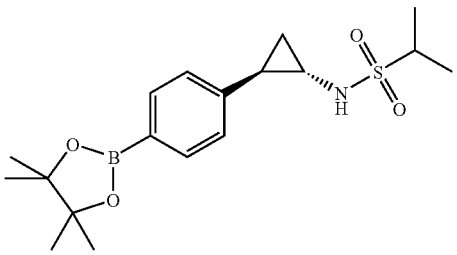

A mixture of potassium acetate (1.02 g, 10.38 mmol), [1,1′-Bis(diphenylphosphino)ferrocene]dichloropalladium (II) complex with dichloromethane (141 mg, 0.173 mmol) and Bis(pinacolato)diboron (1.05 g, 4.15 mmol) were placed in a 250 ml flask and it was flushed with nitrogen. A solution of racemic trans-N-[(-2-(4-bromophenyl)cyclopropyl]-2-propanesulfonamide (Intermediate 6, 1.1 g, 3.46 mmol) in 1,4-dioxane (40 ml) was added, then the reaction mixture was stirred at 80° C. for 4 h and left at room temperature overnight. After concentration in vacuo the residue was partitioned between ethyl acetate and water and the aqueous phase was extracted with ethyl acetate. The combined organic layers were washed with brine, dried over sodium sulphate and evaporated to dryness under reduced pressure to give a brown oil as crude product (2.5 g). The crude preparation was purified twice by flash chromatography (Horizon 40M+) eluting with cyclohexane-ethyl acetate in a ratio of 7:3 to give the title compound (805 mg, 64%).

Alternative Preparation of chiral Trans-N-[2-(4-bromophenyl)cyclopropyl]-2-propanesulfonamide Enantiomer 1 and Enantiomer 2

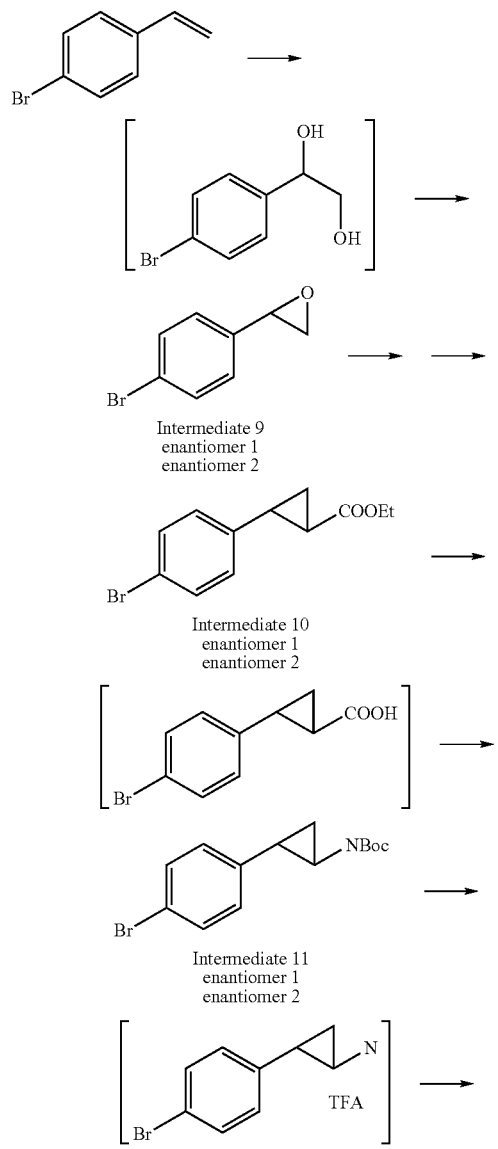

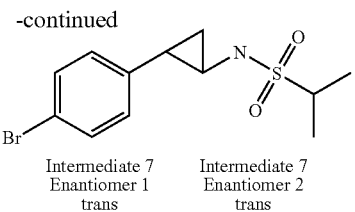

Intermediate 7
Enantiomer 1
trans

Intermediate 7
Enantiomer 2
trans

Intermediate 9, Enantiomer 1: chiral 2-(4-bromophenyl)oxirane Enantiomer 1

A 500 mL round bottom flask, equipped with magnetic stirrer, was charged with 100 mL of ᵗBuOH, 100 mL of water and of AD-mix-β (30.6 g). Stirring at room temperature produced two clear phases; the lower aqueous one appeared bright yellow. The mixture was cooled to 0° C. whereupon some of the dissolved salts precipitated. 4-Br-styrene (4 g, 21.85 mmol) was added at once and the heterogeneous slurry was stirred vigorously at 0° C. for 3 h. While the mixture was stirred at 0° C., solid sodium sulfite (32.8 g) was added and the mixture was allowed to warm to room temperature and stirred for 1 h. 200 mL DCM was added to the reaction mixture and after separation of the layers the aqueous one was further extracted with DCM (3×100 mL). Combined organic extracts were dried over $Na_2SO_4$ and evaporated to dryness to get 4.9 g of crude material as a colourless thick oil.

3.9 g of this oil (17.97 mmol) were dissolved in dry DCM 50 mL, under nitrogen. To this solution trimethylorthacetate (2.962 mL, 23.27 mmol) was added and the mixture cooled down to 0° C. TMS-Cl (2.964 mL, 23.36 mmol) was added dropwise and the reaction mixture left reacting for 1.5 h. The volatiles were evaporated and the residue was dissolved in MeOH, treated with $K_2CO_3$ (3.1 g) and stirred vigorously at room temperature for 3 h. The suspension was filtered, the solid was washed with DCM and the filtrate was evaporated in a rotary evaporator at room temperature under vacuum to get crude title material (3.9 g) that was purified by $SiO_2$ flash chromatography eluting with petroleum ether/$Et_2O$ from 95/5 to 90/10. Evaporation of the solvent afforded title material, 2.95 g, as a colourless oil that became a waxy solid in the fridge.

NMR ($CDCl_3$): 7.49 (d, 2H), 7.13 (d, 2H), 3.84 (dd, 1H), 3.13 (dd, 1H), 2.77 (dd, 1H).
Chiral HPLC: ee 98.6%

Analytical Chiral HPLC Conditions:
column: CHIRALPAK AS-H (25×0.46 cm)
mobile phase: n-Hexane/Ethanol 95/5% v/v
flow rate: 1 ml/min
UV wavelength range: 200-400 nm
Rt Enantiomer 1: 6.1 min 99.3 a/a %
Rt Enantiomer 2: 8.5 min 0.7 a/a %

Intermediate 10 Enantiomer 1: chiral Trans-ethyl 2-(4-bromophenyl)cyclopropanecarboxylate, Enantiomer 1

NaOᵗBu (3.23 g, 33.6 mmol) and 10 mL of dry DME were charged in round bottom flask previously inerted with nitrogen. Triethyl phosphonoacetate (7.7 mL, 38.64 mmol) was added at a rate such to maintain internal temperature below 30° C., about 30 minutes. The mixture was stirred until complete dissolution was observed, about 30 minutes. A solution of chiral 2-(4-bromophenyl)oxirane Enantiomer 1 (Intermediate 9 Enantiomer 1) (3.35 g, 16.8 mmol) in 6 mL of dry DME was added dropwise maintaining internal temperature between 20° C. and 30° C. The reaction mixture was stirred at 60° C. for 24 h. The temperature was increased to 70° C. and maintained at this temperature for further 6 h. Mixture was cooled to room temperature, taken up with 100 mL Et$_2$O, cooled to 0° C. and poured in approx. 80 mL cold ss NH$_4$Cl. The solution was diluted with approx. 20 mL water, the phases were separated and the aqueous one extracted with Et$_2$O 2×100 mL. Combined organics were dried over Na$_2$SO$_4$ and evaporated to dryness to get crude title material that was purified by SiO$_2$ flash chromatography (Horizon 65M) eluting with Et$_2$O/n-hexane 5/95 to get after evaporation of the solvent, pure title material, 3.35 g as a colourless oil.

NMR (CDCl$_3$): 7.40 (d, 2H), 6.98 (d, 2H), 4.18 (q, 2H), 2.48 (m, 1H), 1.87 (m, 1H), 1.61 (M, 1H), 1.29 (t, 3H), 1.28 (m, 1H).

Intermediate 11, Enantiomer 1: chiral
Trans-1,1-dimethylethyl
[2-(4-bromophenyl)cyclopropyl]carbamate
Enantiomer 1

To a solution of chiral trans-ethyl 2-(4-bromophenyl)cyclopropanecarboxylate, Enantiomer 1 (Intermediate 10 Enantiomer 1) (3.3 g, 12.26 mmol) in 50 mL of EtOH, were added 25 mL of 2N NaOH solution and the mixture was stirred vigorously at room temperature for 2 h. Then the mixture was concentrated in vacuo to remove EtOH. 80 mL of water were added and the aqueous phase extracted with Et$_2$O 1×30 mL. The aqueous phase was cooled in an ice bath and acidified with 2N HCl to pH 3 (approx) and extracted with Et$_2$O 3×100 mL. The collected organic phases deriving from extraction of acidic solution were dried over Na$_2$SO$_4$ and concentrated to dryness to get 3 g of crude material as a white solid.

A mixture of this solid (2.97 g, 12.32 mmol) in 40 mL of dry tBuOH, 3 mL of diphenylphosphoryl azide and 2.4 mL of TEA, under nitrogen, was stirred at 90° C. for 48 h and left at room temperature for further 24 h. The solution was concentrated under vacuum and poured into 50 mL of a 10% Na$_2$CO$_3$ solution and 100 mL of Et$_2$O. The phases were separated; the aqueous one diluted with 40 mL of water and extracted with Et$_2$O 3×100 mL. The collected organics were dried over Na$_2$SO$_4$ and evaporated to dryness to get crude title material that was purified by SiO$_2$ flash chromatography (Horizon 65M) eluting with cyclohexane/ethylacetate 85/15. Evaporation of the solvent afforded 2.3 g of pure title material as a white solid.

NMR (CDCl$_3$): 7.38 (d, 2H), 7.03 (d, 2H), 4.82 (bs, 1H), 2.68 (m, 1H), 2.02 (m, 1H), 1.46 (s, 9H), 1.14 (m, 2H).

Intermediate 7, Enantiomer 1 Alternative Procedure:
chiral Trans-N-[2-(4-bromophenyl)cyclopropyl]-2-
propanesulfonamide Enantiomer 1

To a solution of Intermediate 11 Enantiomer 1 (2.3 g, 7.37 mmol) in 50 mL of dry DCM, at 0° C. under nitrogen, 12.5 mL of TFA were added dropwise and stirred at this temperature for 2 h. Reaction mixture was evaporated in vacuo (no heating bath) to get crude material that was left under high vacuum for 4 h to get 3.31 g of a yellow gummy solid.

3.3 g of this solid (10.12 mmol) was suspended in dry DCM 40 mL and the mixture was cooled to −15° C. under nitrogen and TEA (4.24 mL, 30.4 mmol) was added. To the solution were added dropwise 1.2 mL of isopropyl sulphonylchloride (10.12 mmol). The mixture was stirred at this temperature for 2 h. The solution was taken up with DCM 100 mL and 100 mL of water. After phase separation the aqueous one was extracted with DCM 2×100 mL and the collected organic phases were dried over Na$_2$SO$_4$ and concentrated in vacuo to get crude title material as a yellow oil that was purified by SiO$_2$ flash chromatography eluting with cyclohexane/ethyl acetate from 80/20 to 70/30. Evaporation of the solvent afforded 2 g of pure title material as a white solid.

NMR (CDCl$_3$): 7.40 (d, 2H), 7.00 (d, 2H), 4.62 (s, 1H), 3.26 (m, 1H), 2.69 (m, 1H), 2.25 (m, 1H), 1.42 (d, 3H), 1.40 (d, 3H), 1.34 (m, 1H), 1.22 (m, 1H).

Chiral HPLC: ee >99.5%

Analytical Chiral HPLC Conditions:
column: CHIRALPAK AS-H (25×0.46 cm)
mobile phase: n-Hexane/Ethanol 87/13% v/v
flow rate: 0.8 ml/min
DAD: 225 nm
CD: 255 nm
Rt Enantiomer 1: 16.01 min 99.91 a/a %
Rt Enantiomer 2: 18.49 min 0.09 a/a %

Intermediate 9, Enantiomer 2: chiral
2-(4-bromophenyl)oxirane Enantiomer 2

A similar procedure was followed as set out earlier for chiral 2-(4-bromophenyl)oxirane Enantiomer 1 (Intermediate 9 Enantiomer 1) using tBuOH (100 mL), water (100 mL), AD-mix-α (30.6 g), 4-Br-styrene (4 g, 21.85 mmol) and solid sodium sulfite (32.8 g) to give 4.9 g of crude material as a colourless oil.

A similar procedure was followed as set out earlier for chiral 2-(4-bromophenyl)oxirane Enantiomer 1 (Intermediate 9 Enantiomer 1) using this oil (4.9 g, 22.574 mmol), dry DCM (70 mL), trimethylorthacetate (3.72 mL) TMS-Cl (3.724 mL), MeOH (60 mL), and K$_2$CO$_3$ (3.9 g) to give crude title material as an oil that was purified by SiO$_2$ flash chromatography to get after evaporation of the solvent title material, 3.75 g, as a colourless oil that became a waxy solid in the fridge.

NMR (CDCl$_3$): 7.49 (d, 2H), 7.13 (d, 2H), 3.84 (dd, 1H), 3.13 (dd, 1H), 2.77 (dd, 1H).

Chiral HPLC: ee 98.5%

Analytical Chiral HPLC Conditions:
column: CHIRALPAK AS-H (25×0.46 cm)
mobile phase: n-Hexane/Ethanol 95/5% v/v
flow rate: 1 ml/min
UV wavelength range: 200-400 nm
Rt Enantiomer 1: 6.1 min 0.75 a/a %
Rt Enantiomer 2: 8.3 min 99.25 a/a %

Intermediate 10 Enantiomer 2: chiral trans-ethyl
2-(4-bromophenyl)cyclopropanecarboxylate
Enantiomer 2

A similar procedure was followed as set out earlier for chiral trans-ethyl 2-(4-bromophenyl)cyclopropanecarboxylate, Enantiomer 1 (Intermediate 10 Enantiomer 1) using NaOtBu (3.623 g, 37.7 mmol), in dry DME (11.5 mL), triethyl phosphonoacetate (8.6 mL, 43.3 mmol), and chiral 2-(4-bromophenyl)oxirane (Intermediate 9 Enantiomer 2) (3.75 g, 18.84 mmol) in dry DME (7.5 mL) to give approx. 10 g crude title material as a brown oil that was purified by SiO$_2$ flash chromatography to get after evaporation of the solvent, pure title material, 3.45 g as a colourless oil.

NMR (CDCl₃): 7.40 (d, 2H), 6.98 (d, 2H), 4.18 (q, 2H), 2.48 (m, 1H), 1.87 (m, 1H), 1.61 (M, 1H), 1.29 (t, 3H), 1.28 (m, 1H).

Intermediate 11 Enantiomer 2: chiral trans-1,1-dimethylethyl [2-(4-bromophenyl)cyclopropyl]carbamate Enantiomer 2

A similar procedure was followed as set out earlier for chiral trans-1,1-dimethylethyl [2-(4-bromophenyl)cyclopropyl]carbamate Enantiomer 1 (Intermediate 11 Enantiomer 1) using chiral trans-ethyl 2-(4-bromophenyl)cyclopropanecarboxylate Enantiomer 2 (Intermediate 10 Enantiomer 2) (3.4 g, 12.63 mmol) in EtOH (50 mL) and 2N NaOH solution (26 mL) to give 3.15 g of crude material as a white solid.

A similar procedure was followed as set out earlier for trans-1,1-dimethylethyl [2-(4-bromophenyl)cyclopropyl] carbamate Enantiomer 1 (Intermediate 11 Enantiomer 1) using this solid (3.04 g, 12.61 mmol) in dry tBuOH (40 mL), diphenylphosphoryl azide (3 mL) and TEA (2.5 mL) to give crude title material as a yellow gummy solid that was purified by SiO₂ flash chromatography (Horizon 65M) to get after evaporation of the solvent 2.5 g of pure title material as a white solid.

NMR (CDCl₃): 7.38 (d, 2H), 7.03 (d, 2H), 4.82 (bs, 1H), 2.68 (m, 1H), 2.02 (m, 1H), 1.46 (s, 9H), 1.14 (m, 2H).

Intermediate 7 Enantiomer 2 Alternative Procedure: chiral Trans-N-[2-(4-bromophenyl)cyclopropyl]-2-propanesulfonamide Enantiomer 2

A similar procedure was followed as set out earlier for chiral trans-N-[2-(4-bromophenyl)cyclopropyl]-2-propanesulfonamide (Intermediate 7 Enantiomer 1, alternative procedure) using (Intermediate 11 Enantiomer 2) (2.5 g, 8.07 mmol) in dry DCM (50 mL) and TFA (12.5 mL) to give 3.65 g of crude material as a yellow gummy solid.

A similar procedure was followed as set out earlier for chiral trans-N-[2-(4-bromophenyl)cyclopropyl]-2-propanesulfonamide (Intermediate 7 Enantiomer 1, alternative procedure) using 3.65 g of this solid (11.2 mmol) in dry DCM (50 mL), TEA (4.7 mL, 33.6 mmol) and isopropyl sulphonylchloride (1.3 mL) to give crude title material as a yellow oil (3.5 g) that was purified by SiO₂ flash chromatography (Horizon 65M) to get after evaporation of the solvent 2.1 g of pure title material as a white solid.

NMR (CDCl₃): 7.40 (d, 2H), 7.00 (d, 2H), 4.62 (s, 1H), 3.26 (m, 1H), 2.69 (m, 1H), 2.25 (m, 1H), 1.42 (d, 3H), 1.40 (d, 3H), 1.34 (m, 1H), 1.22 (m, 1H).

Chiral HPLC: ee >98.5%

Analytical Chiral HPLC Conditions:
column: CHIRALPAK AS-H (25×0.46 cm)
mobile phase: n-Hexane/Ethanol 87/13% v/v
flow rate: 0.8 ml/min
DAD: 225 nm
CD: 255 nm
Rt Enantiomer 1: 16.07 min 0.74 a/a %
Rt Enantiomer 2: 18.44 min 99.26 a/a %

Intermediate 12 Enantiomer 1: Trans-N-{2-[4-(4,4,5,5-tetramethyl-1,3,2-dioxaborolan-2-yl)phenyl]cyclopropyl}-2-propanesulfonamide (Enantiomer 1)

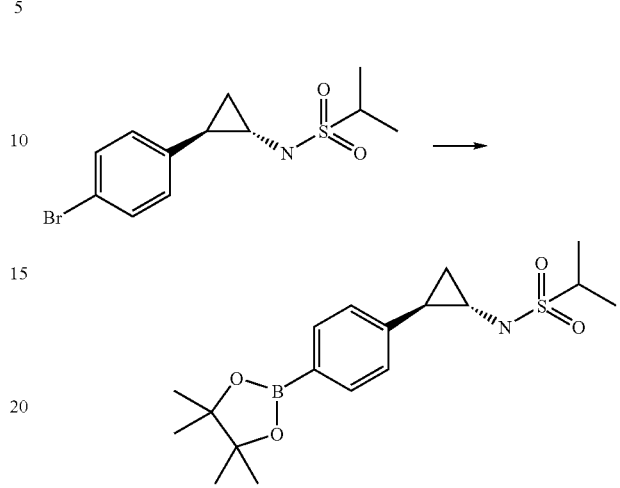

N-[2-(4-bromophenyl)cyclopropyl]-2-propanesulfonamide Enantiomer 1 (Intermediate 7, Enantiomer 1) (155 mg, 0.487 mmol) was dissolved in dry 1,4-dioxane (6 ml). Potassium acetate (143 mg, 1.46 mmol, 3 eq), 1,1'-Bis(diphenylphosphino)ferrocene-palladium(II)dichloride (20 mg, 0.024 mmol, 0.05 eq) and bis(pinacolato)diboron (148 mg, 0.584 mmol, 1.2 eq) were added to the solution under nitrogen at room temperature. The reaction mixture was heated at 80° C. for 4 h with stirring and then left overnight at r.t.

The solvent was evaporated and the residue dissolved in ethyl acetate/water. The organic layer was separated, dried and concentrated. The crude product was purified by flash chromatography, eluting with cyclohexane/ethyl acetate 80:20, to give the title compound as a yellow oil (139 mg, 78% yield).

¹HNMR (DMSO) δ: 7.65 (1H, s), 7.55 (2H, d), 7.10 (2H, d), 3.25 (1H, m), 2.60 (1H, m), 2.10 (1H, m), 1.3-1.15 (20H, multiple signals overlapping).

LC-MS: Rt 2.61 min, MS found 383 (M+NH₄⁺), C₁₈H₂₈BNO₄S requires 365.

Analytical Chromatographic Conditions for Intermediate 12

| Analytical chromatographic conditions for Intermediate 12 | |
|---|---|
| Column: | Supelcosil ABZ + Plus 3 μm, 33 × 4.6 mm |
| Mobile phase: | A: H₂O + 0.1% HCOOH; B: CH₃CN |
| Gradient: | 0% to 95% B in 3 min, 95% B for 1 min, 95% to 0% B in 0.1 min |
| Flow rate: | 2 ml/min |
| UV wavelength range: | 200-400 nm |
| Mass range: | 100-1000 amu |
| Ionization: | ES+ |

Intermediate 12 Enantiomer 1 Alternative Procedure: Trans-N-{2-[4-(4,4,5,5-tetramethyl-1,3,2-dioxaborolan-2-yl)phenyl]cyclopropyl}-2-propanesulfonamide (Enantiomer 1)

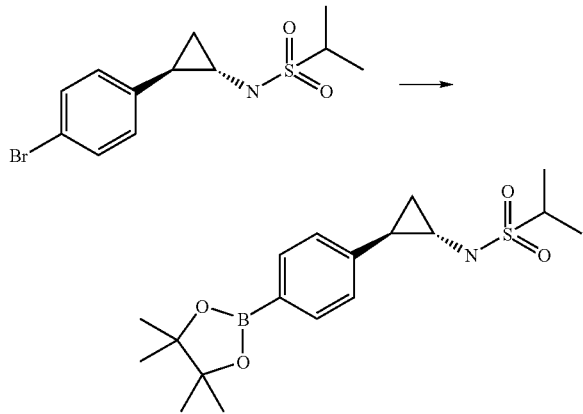

N-[2-(4-bromophenyl)cyclopropyl]-2-propanesulfonamide (Enantiomer 1) (1.5 g, 4.7 mmol) was dissolved in 1,4-dioxane (50 ml). Potassium acetate (1.85 g, 18.8 mmol, 3 eq), 1,1'-Bis(diphenylphosphino)ferrocene-palladium(II)dichloride (192 mg, 0.23 mmol, 0.05 eq) and bis(pinacolato)diboron (1.43 g, 5.64 mmol, 1.2 eq) were added to the solution. The reaction mixture was heated at 90° C. for 5 hrs with stirring. After cooling, the solvent was evaporated under reduced pressure and the residue was dissolved in ethyl acetate and washed with water. The organic layer was separated, dried over $Na_2SO_4$ and concentrated. The crude product was purified by flash chromatography, eluting with cyclohexane/ethyl acetate 80:20, to give the title compound as a yellow oil (1.35 g, purity ~50% according to NMR analysis, the main impurity being the bromide starting material).

$^1$HNMR (DMSO) δ: 7.65 (1H, s), 7.55 (2H, d), 7.10 (2H, d), 3.25 (1H, m), 2.60 (1H, m), 2.10 (1H, m), 1.3-1.15 (20H, multiple signals overlapping).

Intermediate 12 Enantiomer 2: Trans-N-{2-[4-(4,4,5,5-tetramethyl-1,3,2-dioxaborolan-2-yl)phenyl]cyclopropyl}-2-propanesulfonamide (Enantiomer 2)

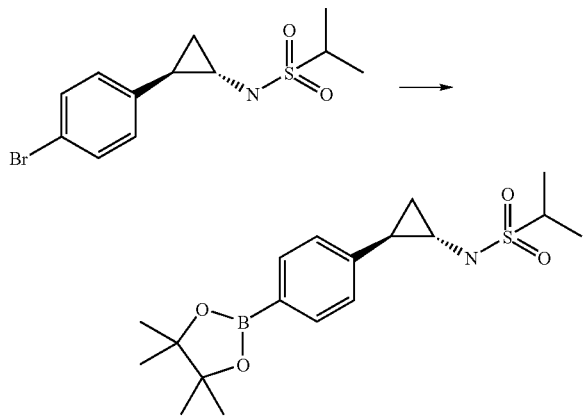

A similar procedure was followed as set out above for trans-N-{2-[4-(4,4,5,5-tetramethyl-1,3,2-dioxaborolan-2-yl)phenyl]cyclopropyl}-2-propanesulfonamide Enantiomer 1 (Intermediate 12 Enantiomer 1) using trans-N-[2-(4-bromophenyl)cyclopropyl]-2-propanesulfonamide Enantiomer 2 (Intermediate 7, Enantiomer 2) (155 mg, 0.487 mmol) in dry 1,4-dioxane (6 ml), potassium acetate (143 mg, 1.46 mmol, 3 eq), 1,1'-Bis(diphenylphosphino)ferrocene-palladium(II)dichloride (20 mg, 0.024 mmol, 0.05 eq) and bis (pinacolato)diboron (148 mg, 0.584 mmol, 1.2 eq) to give crude product which was purified to give the title compound as a colourless oil (144 mg, 81% yield).

$^1$HNMR (DMSO) δ: 7.65 (1H, s), 7.55 (2H, d), 7.10 (2H, d), 3.25 (1H, m), 2.65 (1H, m), 2.10 (1H, m), 1.35-1.15 (20H, multiple signals overlapping).

LC-MS: Rt 2.62 min, MS found 383 (M+$NH_4^+$), $C_{18}H_{28}BNO_4S$ requires 365.

Intermediate 12 Enantiomer 2 Alternative Procedure: Trans-N-{2-[4-(4,4,5,5-tetramethyl-1,3,2-dioxaborolan-2-yl)phenyl]cyclopropyl}-2-propanesulfonamide (Enantiomer 2)

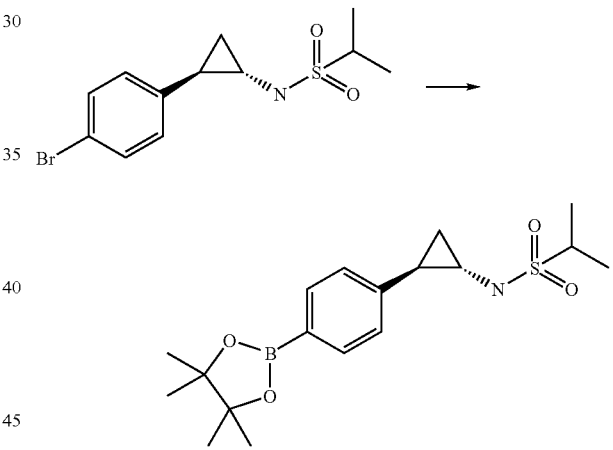

A similar procedure was followed as set out above for trans-N-{2-[4-(4,4,5,5-tetramethyl-1,3,2-dioxaborolan-2-yl)phenyl]cyclopropyl}-2-propanesulfonamide (Enantiomer 1) (Intermediate 12 Enantiomer 1 alternative procedure) using N-[2-(4-bromophenyl)cyclopropyl]-2-propanesulfonamide (Enantiomer 2) (1.5 g, 4.7 mmol) in 1,4-dioxane (50 mL), potassium acetate (1.85 g, 18.8 mmol, 3 eq), 1,1'-Bis(diphenylphosphino)ferrocene-palladium(II)dichloride (192 mg, 0.23 mmol, 0.05 eq) and bis(pinacolato)diboron (1.43 g, 5.64 mmol, 1.2 eq) to give crude product which was purified by flash chromatography, eluting with cyclohexane/ethyl acetate 80:20, to give the title compound as a yellow oil (1.5 g, purity ~50% according to NMR analysis, the main impurity being the bromide starting material).

$^1$HNMR (DMSO) δ: 7.65 (1H, s), 7.55 (2H, d), 7.10 (2H, d), 3.25 (1H, m), 2.60 (1H, m), 2.10 (1H, m), 1.3-1.15 (20H, multiple signals overlapping).

Example 1

Trans-N-{-2-[4-(6-fluoro-3-pyridinyl)phenyl]cyclopropyl}-2-propanesulfonamide racemic

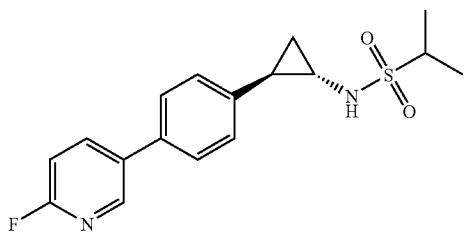

A mixture of trans-N-[(-2-(4-chlorophenyl)cyclopropyl]-2-propanesulfonamide racemic (Intermediate 1) (130 mg, 0.48 mmol), (6-fluoro-3-pyridinyl)boronic acid (100 mg, 0.71 mmol) and potassium fluoride (90 mg, 1.43 mmol) in dry tetrahydrofuran (5 ml) was degassed with argon for 5 minutes. Then palladium acetate (5 mg, 0.024 mmol), and 2-(di-tert-butylphosphino)biphenyl (13 mg, 0.043 mmol) were added and the whole mixture heated at 140° C. in a microwave reactor for 10 minutes. The reaction mixture was allowed to cool to 20° C. and then partitioned between ethyl acetate and water. The organic layer was dried over sodium sulphate and evaporated in vacuo to give approx. 0.1 g of a brown oil. The crude product was chromatographed on a 5 g isolute silica Sep-Pak® column eluting from 0-50% ethyl acetate in petroleum ether to give a yellow oil (approximately 30 mg). The chromatographed product was analysed and gave: mass spectrum (API+): Found 335 (MH$^+$); $C_{17}H_{19}FN_2O_2S$ requires 334; $^1$H-NMR (400 MHz, CDCl$_3$): 1.28 (2H, m), 1.42 (6H, m), 2.32 (1H, m), 2.77 (1H, m), 3.28 (1H, m), 4.69 (1H, m), 7.00 (1H, m), 7.21 (2H, m), 7.45 (2H, m), 7.94 (1H, m), 8.39 (1H, m).

The product was then dissolved in DCM and treated with 1M HCl in ether and blown down. The residue was triturated in 1M HCl in ether (2×2 ml), decanted and dried to give the title compound as a brown solid (21 mg, 12%).

Examples 2 to 9

Example compounds 2 to 9 were prepared in an array using the protocol described below. The described protocol is for Example 2, Trans-N-{-2-[4-(6-methyl-3-pyridinyl)phenyl]cyclopropyl}-2-propanesulfonamide. Examples 3 to 9 were prepared in analogous fashion using the appropriate bromoaryl reagent. Example 1 was also reprepared by this method.

Example 2

Trans-N-{-2-[4-(6-methyl-3-pyridinyl)phenyl]cyclopropyl}-2-propanesulfonamide racemic

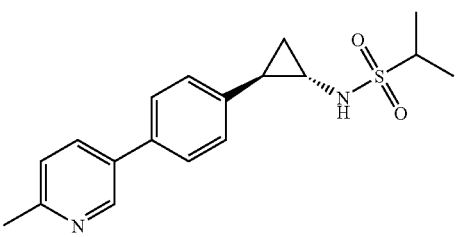

In an 8 ml vial (PLS apparatus) the bromoaryl reagent (3-bromo-6-methylpyridine for Example 2) (0.328 mmol) was placed together with a solution of trans-N-{2-[4-(4,4,5,5-tetramethyl-1,3,2-dioxaborolan-2-yl)phenyl]cyclopropyl}-2-propanesulfonamide (Intermediate 8) (60 mg, 0.164 mmol) in dry 1,4-dioxane (1.0 ml). Polymer supported Tetrakis catalyst (Pol-Pd(PPh$_3$)$_4$) (15 mg, 0.00164 mmol), and Na$_2$CO$_3$ 2M (0.205 ml, 0.41 mmol) were added. The reaction mixture was shaken at 90° C. for 3-4 h (if reaction not complete by LC/MS analysis then heated for an additional 3 h) then left at room temperature overnight. The resin was filtered off (by Alltech filter tube) and washed with dichloromethane, water, methanol and dichloromethane. The liquid phase was evaporated until dryness under reduced pressure and the residue was taken up in dichloromethane (2 ml) and washed with HCl 1M (1 ml) then the acidic solution was basified with K$_2$CO$_3$ 2M and extracted with dichloromethane (2×1 ml). The combined organic extracts were concentrated under reduced pressure to give a crude oil which was purified by reverse phase HPLC to give the title compound. The HPLC conditions were as given in "Preparative Chromatography" above.

Examples 1 to 9 as synthesised by this route are summarised in Table 1

TABLE 1

| Ex | Structure | Name | LC/MS (min) | Yield |
|---|---|---|---|---|
| 1 | 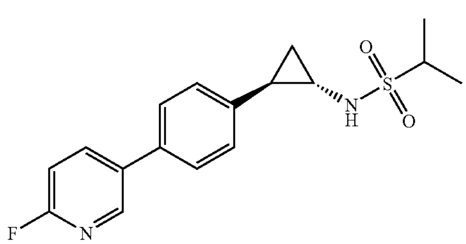 | Trans-N-{-2-[4-(6-fluoro-3-pyridinyl)phenyl]cyclopropyl}-2-propanesulfonamide racemic | 3.77 335 [M + H]+ | 50% |

TABLE 1-continued

| Ex | Structure | Name | LC/MS (min) | Yield |
|---|---|---|---|---|
| 2 | 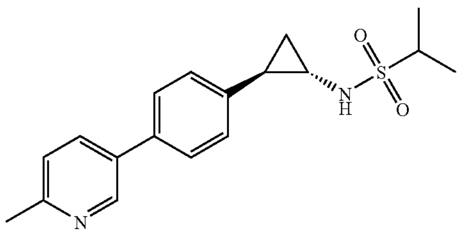 | Trans-N-{-2-[4-(6-methyl-3-pyridinyl)phenyl]cyclopropyl}-2-propanesulfonamide racemic | 3.31 331 [M + H]+ | 13% |
| 3 | 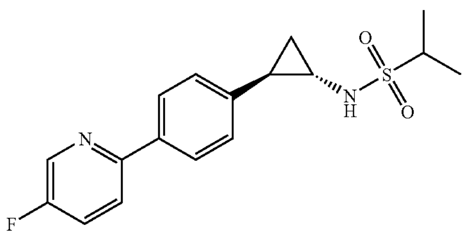 | Trans-N-{-2-[4-(5-fluoro-2-pyridinyl)phenyl]cyclopropyl}-2-propanesulfonamide racemic | 3.53 335 [M + H]+ | 9% |
| 4 | 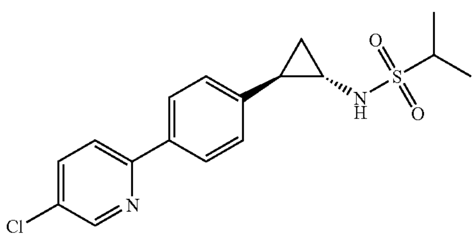 | Trans-N-{-2-[4-(5-chloro-2-pyridinyl)phenyl]cyclopropyl}-2-propanesulfonamide racemic | 3.85 351 [M + H]+ | 3% |
| 5 | 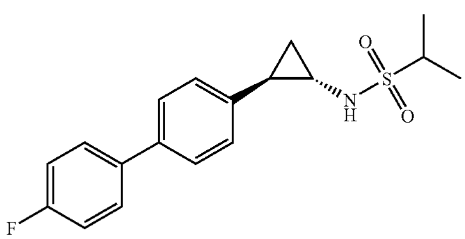 | Trans-N-{-2-[4-(5-fluoro-phenyl)phenyl]cyclopropyl}-2-propanesulfonamide racemic | 4.05 351 [M + NH4]+ | 2% |
| 6 | 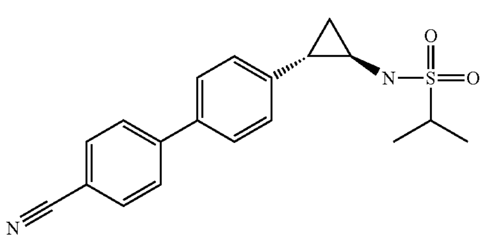 | Trans-N-{-2-[4-(4-cyano-phenyl)phenyl]cyclopropyl}-2-propanesulfonamide racemic | 3.97 339 [M − H] | 17% |
| 7 | 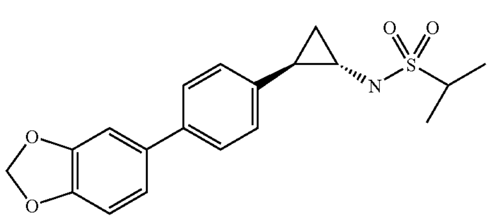 | Trans-N-{2-[4-(1,3-benzodioxol-5-yl)phenyl]cyclopropyl}-2-propanesulfonamide racemic | 3.88 377 [M + NH4]+ | 3% |

TABLE 1-continued

| Ex | Structure | Name | LC/MS (min) | Yield |
|---|---|---|---|---|
| 8 | 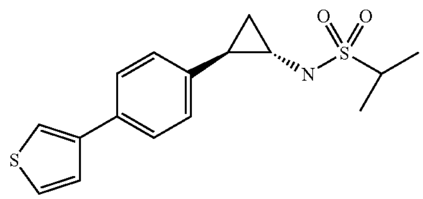 | Trans-N-{-2-[3-(thienyl)phenyl]cyclopropyl}-2-propanesulfonamide racemic | 3.87 339 [M + NH4]+ | 9% |
| 9 | 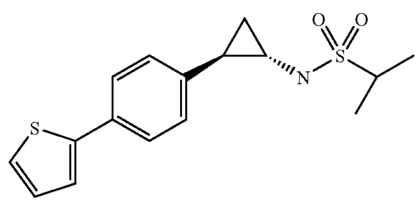 | Trans-N-{-2-[2-(thienyl)phenyl]cyclopropyl}-2-propanesulfonamide racemic | 3.93 339 [M + NH4]+ | 21% |

Example 10

Trans-N-{-2-[4-(5-fluoro-3-pyridinyl)phenyl]cyclopropyl}-2-propanesulfonamide racemic A similar procedure was followed as set out above for trans-N-{-2-[4-(6-methyl-3-pyridinyl)phenyl]cyclopropyl}-2-propanesulfonamide racemic (Example 2) using 3-bromo-5-fluoropyridine (66.5 mg, 0.378 mmol), trans-N-{2-[4-(4,4,5,5-tetramethyl-1,3,2-dioxaborolan-2-yl)phenyl] cyclopropyl}-2-propanesulfonamide (Intermediate 8) (69 mg, 0.189 mmol) in dry 1,4-dioxane (1.0 ml), polymer supported Tetrakis palladium catalyst (Pol-Pd(PPh$_3$)$_4$) (51 mg, 0.00567 mmol) and Na$_2$CO$_3$ 2M (0.236 ml, 0.472 mmol) to give a crude product which was purified by reverse phase HPLC to give the title compound. The HPLC conditions were as given in "Preparative Chromatography" above.

$^1$H-NMR (400 MHz, CDCl$_3$): 1.31 (1H, m), 1.41 (1H, m), 1.42 (3H, d), 1.44 (3H, d), 2.35 (1H, m), 2.78 (1H, m), 3.30 (1H, m), 4.65 (1H, s), 7.23 (2H, d), 7.51 (2H, d), 7.57 (1H, td), 8.44 (1H, s), 8.64 (1H, s).

LC/MS: RT=2.52, observed [M+H]$^+$=335.

Example 11

Trans-N-{-2-[4-(5-methyl-3-pyridinyl)phenyl]cyclopropyl}-2-propanesulfonamide racemic

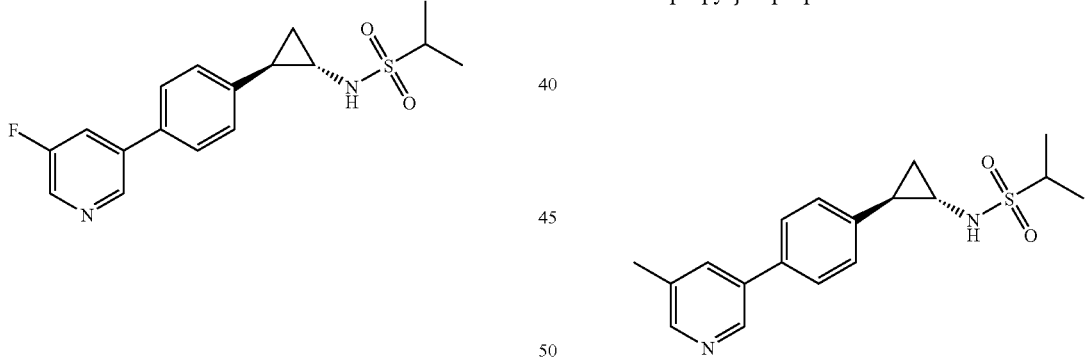

Example 11 was prepared from trans-N-{2-[4-(4,4,5,5-tetramethyl-1,3,2-dioxaborolan-2-yl)phenyl]cyclopropyl}-2-propanesulfonamide (Intermediate 8) (69 mg, 0.189 mmol) and 3-bromo-5-methylpyridine (65 mg, 0.378 mmol) according to a similar procedure as for Example 10.

$^1$H-NMR (400 MHz, CDCl$_3$): 1.34 (2H, m), 1.40 (3H, d), 1.45 (3H, d), 2.32 (1H, m), 2.40 (3H, s), 2.76 (1H, m), 3.27 (1H, m), 4.63 (1H, s), 7.20 (2H, d), 7.60 (2H, m), 7.88 (2H, d), 8.53 (1H, m).

LC/MS: RT=2.61, observed [M+H]$^+$=331.

Example 12

Enantiomer 1: Trans-N-{N-{2-[4-(5-fluoro-3-pyridinyl)phenyl]cyclopropyl}-2-propanesulfonamide Enantiomer 1

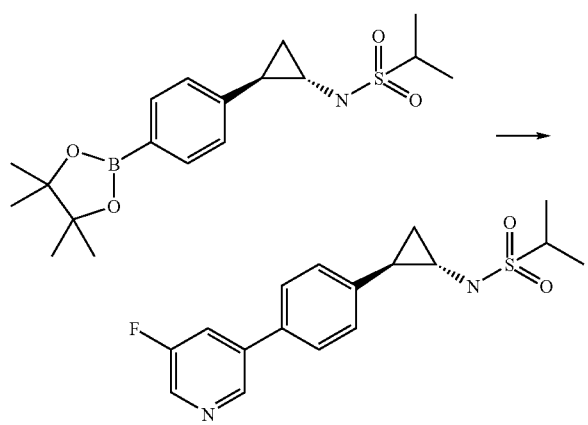

The Example 12 compounds are the single enantiomer compounds of Example 10.

Trans-N-{(1S,2R)-2-[4-(4,4,5,5-tetramethyl-1,3,2-dioxaborolan-2-yl)phenyl]cyclopropyl}-2-propanesulfonamide Enantiomer 1 (Intermediate 12 Enantiomer 1) (139 mg, 0.38 mmol) was dissolved in dioxane (3 ml) in a 8 ml vial. Polymer supported Tetrakis palladium catalyst (Pol-Pd(PPh$_3$)$_4$) (104 mg, 0.0114 mmol, 0.03 eq, loading 0.11 mmol/g), 2M Na$_2$CO$_3$ aqueous solution (0.48 ml, 0.95 mmol, 2.5 eq) and 3-bromo-5-fluoropyridine (134 mg, 0.76 mmol, 2 eq) were added. The vial was shaken at 80° C. for 4 hours and then left still overnight at room temperature.

The reaction mixture was filtered and the resin washed with dichloromethane (3 ml), methanol (3 ml), dichloromethane (3 ml) and methanol (3 ml). The solution was concentrated and the residue dissolved in dichloromethane and washed with water. The organic layer was separated, dried and concentrated. The crude was purified via reverse phase mass directed preparative HPLC to give the title compound (10.9 mg, 8.6% yield).

$^1$HNMR (CDCl$_3$) δ: 8.65 (1H, s), 8.45 (1H, s), 7.60 (1H, d), 7.50 (2H, d), 7.30 (2H, d), 4.80 (1H, s), 3.30 (1H, m), 2.80 (1H, m), 2.35 (1H, m), 1.45 (7H, m), 1.30 (1H, m).

LC-MS: Rt 2.475 min, MS found 335 (M$^+$), C$_{17}$H$_{19}$FN$_2$O$_2$S requires 334.

Chiral HPLC: Rt 15.31 min, area % 97.8 (DAD at 225 nm).

Preparative Chromatographic Conditions for Example 12

| Preparative chromatographic conditions for Example 12 | |
|---|---|
| Column: | XTerra prep MS C18 5 µm, 100 × 19 mm |
| Mobile phase: | A: NH$_4$HCO$_3$ sol. 10 mM, pH10; B: CH$_3$CN |
| Gradient: | 10% (B) for 1 min, from 10% (B) to 95% (B) in 12 min, 95% (B) for 3 min, from 95% (B) to 10% (B) in 0.1 min |
| Flow rate: | 20 ml/min |
| UV wavelength range: | 210-350 nm |
| Mass range: | 100-900 amu |
| Ionization: | ES+ |

Analytical Chiral Chromatographic Conditions for Example 12

| Analytical Chiral chromatographic conditions for Example 12 | |
|---|---|
| Column: | Chiralpak AS-H, 25 × 4.6 mm |
| Mobile phase: | n-Hexane 70%, ethanol 30% |
| Flow rate: | 0.8 ml/min |
| UV wavelength range: | 210-340 nm |

Example 12

Enantiomer 2: Trans-N-{2-[4-(5-fluoro-3-pyridinyl)phenyl]cyclopropyl}-2-propanesulfonamide Enantiomer 2

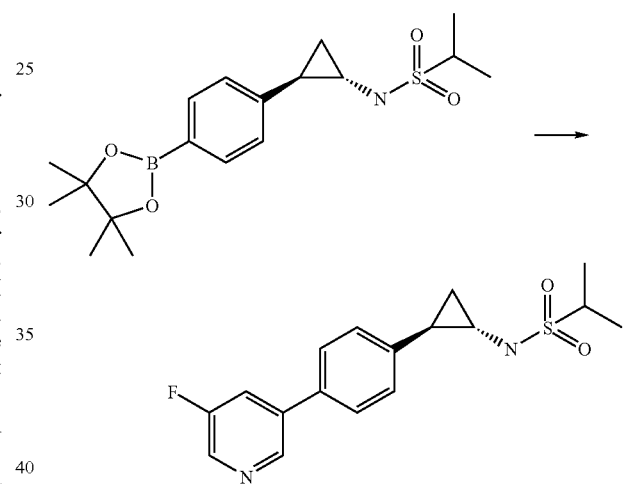

A similar procedure was followed as set out above for trans-N-{2-[4-(5-fluoro-3-pyridinyl)phenyl]cyclopropyl}-2-propanesulfonamide Enantiomer 2 (Example 12 Enantiomer 2) using trans-N-{(1S,2R)-2-[4-(4,4,5,5-tetramethyl-1,3,2-dioxaborolan-2-yl)phenyl]cyclopropyl}-2-propanesulfonamide Enantiomer 2 (Intermediate 12 Enantiomer 2) (139 mg, 0.38 mmol) to give crude product which was purified via reverse phase mass directed preparative HPLC to give the title compound (9.6 mg, 7.6% yield).

$^1$HNMR (CDCl$_3$) δ: 8.65 (1H, s), 8.45 (1H, s), 7.60 (1H, d), 7.50 (2H, d), 7.30 (2H, d), 4.75 (1H, s), 3.30 (1H, m), 2.80 (1H, m), 2.35 (1H, m), 1.40 (7H, m), 1.30 (1H, m).

LC-MS: Rt 2.46 min, MS found 335 (M$^+$), C$_{17}$H$_{19}$FN$_2$O$_2$S requires 334.

Chiral HPLC: Rt 11.635 min, area % 84.8 (DAD at 225 nm).

It is noteworthy that the Example 12 Enantiomer 2 compound (the compound prepared from Intermediate 7 Enantiomer 2—i.e. the longer retention time Intermediate 7 enantiomer) has a shorter retention time under very similar chiral HPLC conditions (the same chiral column and slightly different solvent conditions).

Chiral Array Examples 13 to 25

Chiral Example Compounds 13 to 25 were prepared in arrays from Enantiomer 1 starting material, Enantiomer 2 starting material or both.

General Procedure for Example Compounds Prepared from Enantiomer 1 Starting Material

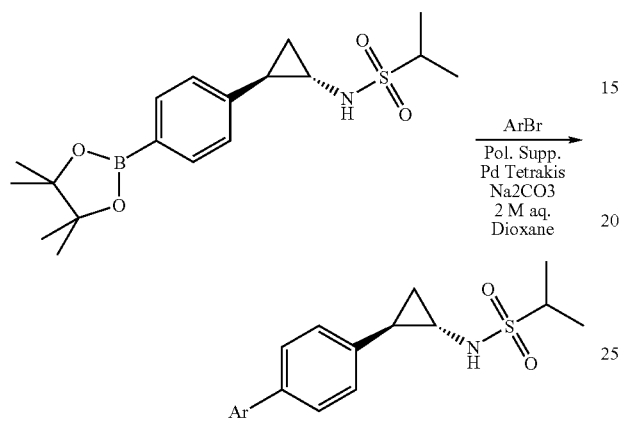

The array was carried out in 8 ml Wheaton vials with Teflon lined screw cap. 165 μl of a 2M Na$_2$CO$_3$ aqueous solution were added to the vial containing the aryl bromide (0.232 mmol) and polymer supported Pd Tetrakis (Aldrich, 2.5 mg, loading ~0.5 mmol/g). Then a solution of N-{2-[4-(4,4,5,5-tetramethyl-1,3,2-dioxaborolan-2-yl)phenyl]cyclopropyl}-2-propanesulfonamide Enantiomer 1 (48 mg) (Intermediate 12 Enantiomer 1, containing ~50% of the corresponding starting material bromide as impurity, estimated by LC-MS and 1H-NMR) in 1 ml of dioxane was added and the vial was shaken at 90° C. for 5 hours and finally left still for 9 hours.

The next day the reaction was worked up, adding 0.5 ml of 2M HCl aqueous solution and shaking 20 minutes at room temperature. After that time, MeOH (1 ml) was added and the resulting clear solution was filtered through a small celite pad, to remove the catalyst. The celite was washed with further MeOH (1 ml) and the collected solution was evaporated first by nitrogen flow and then with SpeedVac vacuum centrifuge.

The crude product was purified via reverse phase mass directed preparative HPLC. The fractions containing the product were evaporated with SpeedVac vacuum centrifuge.

Analytical Chromatographic Conditions for Chiral Array Examples 13 to 25

| Analytical chromatographic conditions for Chiral Array Examples 13 to 25 | |
|---|---|
| Column: | Gemini C18, 50 × 4.6 mm, 5 μm |
| Mobile phase: | A: NH$_4$HCO$_3$ sol. 10 mM, pH10; B: CH$_3$CN |
| Gradient: | 35% (B) for 0.5 min, 35% (B) → 95% (B) in 4.5 min, 95% (B) for 1.5 min |
| Flow rate: | 2 ml/min |
| UV wavelength range: | 210-350 nm |
| Ionization: | ES+/ES− |
| Mass range: | 100-900 amu |

Preparative Chromatographic Conditions

| Preparative chromatographic conditions | |
|---|---|
| Column: | Gemini C18, 100 × 21 mm, 5 μm |
| Mobile phase: | A: NH$_4$HCO$_3$ sol. 10 mM, pH10; B: CH3CN |
| Gradient 1: | 35% (B) for 1 min, 35% (B) → 60% (B) in 9 min, 60% (B) → 100% (B) in 2 min, 100% (B) for 4 min |
| Gradient 2: | 35% (B) for 1 min, 35% (B) → 70% (B) in 9 min, 70% (B) → 100% (B) in 2 min, 100% (B) for 4 min |
| Gradient 3: | 50% (B) for 1 min, 50% (B) → 85% (B) in 9 min, 85% (B) → 100% (B) in 2 min, 100% (B) for 4 min |
| Flow rate: | 17 ml/min |
| UV wavelength range: | 210-350 nm |
| Ionization: | ES+/ES− |
| Mass range: | 100-900 amu (ES+)/100-700 amu (ES−) |

The gradient used for each example was as indicated in the table below.

General Procedure for Example Compounds Prepared from Enantiomer 2 Starting Material

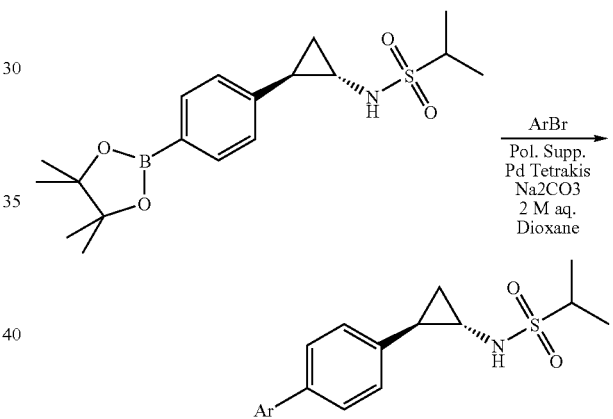

The array was carried out in 8 ml Wheaton vials with Teflon lined screw cap. 182 μl of a 2M Na$_2$CO$_3$ aqueous solution, the aryl bromide (0.293 mmol) and polymer supported Pd Tetrakis (Aldrich, 2.9 mg, loading ~0.5 mmol/g) were added to a solution of N-{2-[4-(4,4,5,5-tetramethyl-1,3,2-dioxaborolan-2-yl)phenyl]cyclopropyl}-2-propanesulfonamide Enantiomer 2 (53 mg) (Intermediate 12 Enantiomer 2 containing ~50% of the corresponding starting material bromide as impurity, estimated by LC-MS and $^1$H-NMR) in 1 ml of dioxane. The vial was shaken at 90° C. for 5 hours and finally left still overnight at room temperature.

The next day the reaction was worked up, adding 0.5 ml of 2M HCl aqueous solution. The resulting clear solution was filtered through a small celite pad, to remove the catalyst. The celite was washed with MeOH (2 ml) and the collected solution was evaporated first by nitrogen flow and then with SpeedVac vacuum centrifuge.

The crude product was purified via reverse phase mass directed preparative HPLC. The fractions containing the product were evaporated with SpeedVac vacuum centrifuge.

The Analytical and preparative chromatographic conditions were as above for the Enantiomer 1 compounds The compounds of Examples 13 to 25 shown in Table 2 were synthesised according to these procedures using the appropriate aryl bromide starting material. The aryl bromide starting materials were obtained from commercial sources. The nomenclature used is that a compound prepared from Enantiomer 1 starting material (the starting material derived from the faster running Intermediate 7 material under the conditions described in Intermediate 7) is named Enantiomer 1 product. It need not be the faster running product. The retention time shown in the table is that obtained under the analytical conditions given above.

Certain of the chiral compounds in the table below are single enantiomers of the compounds of certain of the racemic compound Examples described above. Example 13 describes two single enantiomers of Example 1; Example 14 describes two single enantiomers of Example 3; Example 15 describes two single enantiomers of Example 4; Example 16 describes two single enantiomers of Example 5; Example 17 describes a single enantiomer of Example 6; Example 18 describes a single enantiomer of Example 7; Example 19 describes two single enantiomers of Example 11. The two Example 12 enantiomers were resynthesised in the array.

TABLE 2

| Ex No | Structure | MS ESI+ MH+ [MNH4+] | MS ESI− (M − H)− | Purity (%) | Ret. Time (min) | Prep. Gradient | Name |
|---|---|---|---|---|---|---|---|
| 12 Enant 1 | 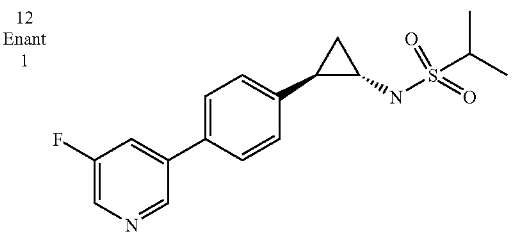 | 334.99 | 332.97 | 95 | 2.3 | 1 | Trans-N-{2-[4-(5-fluoro-3-pyridinyl)phenyl]cyclopropyl}-2-propanesulfonamide Enantiomer 1 |
| 12 Enant 2 | 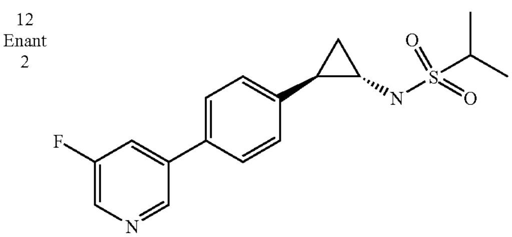 | 335.02 | 332.97 | 1.2 | 2.29 | 1 | Trans-N-{2-[4-(5-fluoro-3-pyridinyl)phenyl]cyclopropyl}-2-propanesulfonamide Enantiomer 2 |
| 13 Enant 1 | 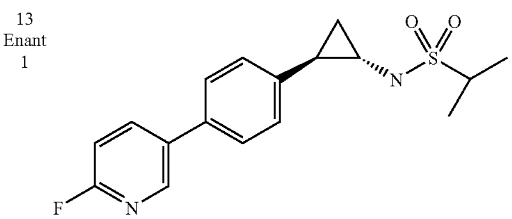 | 334.98 | 332.97 | 97 | 2.52 | 1 | Trans-N-{2-[4-(6-fluoro-3-pyridinyl)phenyl]cyclopropyl}-2-propanesulfonamide Enantiomer 1 |
| 13 Enant 2 | 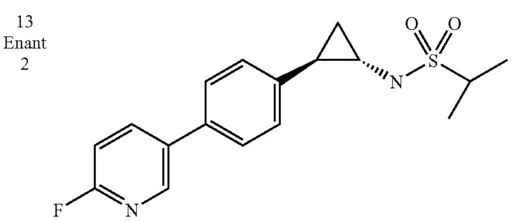 | 335.05 | 333.04 | 80 | 2.52 | 1 | Trans-N-{2-[4-(6-fluoro-3-pyridinyl)phenyl]cyclopropyl}-2-propanesulfonamide Enantiomer 2 |
| 14 Enant 1 | 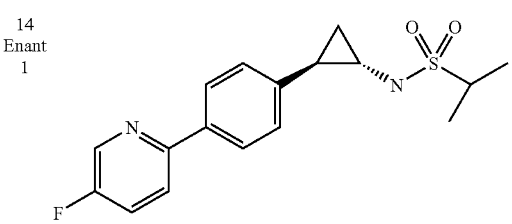 | 335.02 | 333.02 | 95 | 2.58 | 1 | Trans-N-{2-[4-(5-fluoro-2-pyridinyl)phenyl]cyclopropyl}-2-propanesulfonamide Enantiomer 1 |

TABLE 2-continued

| Ex No | Structure | MS ESI+ MH+ [MNH4+] | MS ESI− (M − H)− | Purity (%) | Ret. Time (min) | Prep. Gradient | Name |
|---|---|---|---|---|---|---|---|
| 14 Enant 2 | 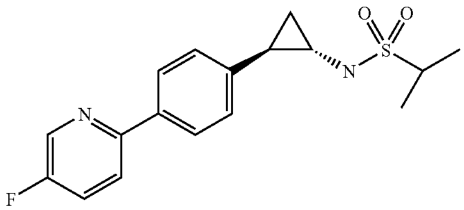 | 334.96 | 332.97 | 96 | 2.57 | 1 | Trans-N-{2-[4-(5-fluoro-2-pyridinyl)phenyl]cycloprop-yl}-2-propanesulfonamide Enantiomer 2 |
| 15 Enant 1 | 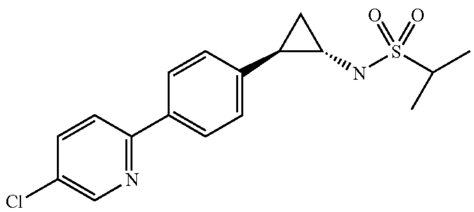 | 350.95, 352.93 | 348.96, 350.96 | 95 | 3.05 | 1 | Trans-N-{2-[4-(5-chloro-2-pyridinyl)phenyl]cycloprop-yl}-2-propanesulfonamide Enantiomer 1 |
| 15 Enant 2 | 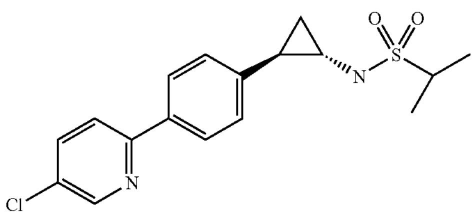 | 350.95, 352.98 | 349.00, 350.95 | 88 | 3.05 | 1 | Trans-N-{2-[4-(5-chloro-2-pyridinyl)phenyl]cycloprop-yl}-2-propanesulfonamide Enantiomer 2 |
| 16 Enant 1 | 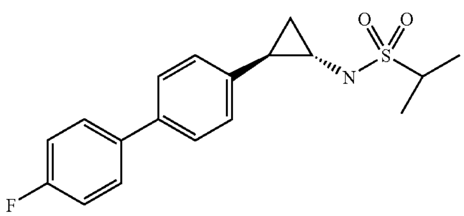 | — | 332.10 | 89 | 3.35 | 2 | Trans-N-[2-(4′-fluoro-4-biphenylyl)cyclopropyl]-2-propanesulfonamide Enantiomer 1 |
| 16 Enant 2 | 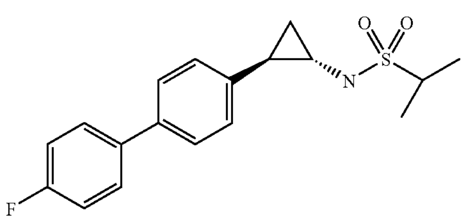 | 333.96 [351.01] | 331.95 | 99 | 3.36 | 2 | Trans-N-[2-(4′-fluoro-4-biphenylyl)cyclopropyl]-2-propanesulfonamide Enantiomer 2 |
| 17 Enant 1 | 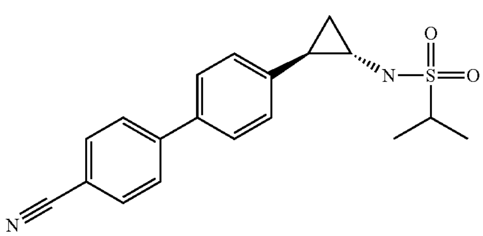 | [358.05] | 339.05 | 70 | 2.97 | 1 | Trans-N-[2-(4′-cyano-4-biphenylyl)cyclopropyl]-2-propanesulfonamide Enantiomer 1 |

TABLE 2-continued

| Ex No | Structure | MS ESI+ MH+ [MNH4+] | MS ESI− (M − H)− | Purity (%) | Ret. Time (min) | Prep. Gradient | Name |
|---|---|---|---|---|---|---|---|
| 18 Enant 2 | 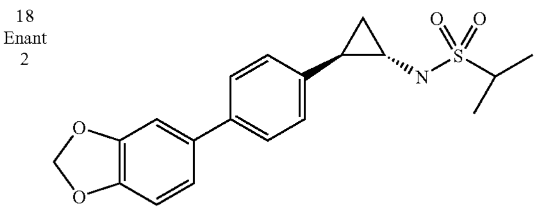 | 359.98, 377.04 | 358.01 | 99 | 3.15 | 2 | Trans-N-{2-[4-(1,3-benzodioxol-5-yl)phenyl]cyclopropyl}-2-propanesulfonamide Enantiomer 2 |
| 19 Enant 1 | 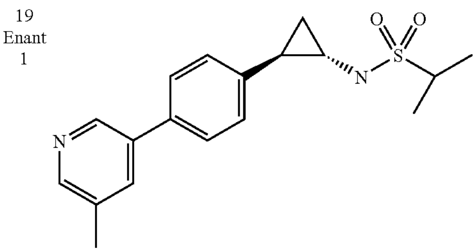 | 331.06 | 329.03 | 78 | 2.52 | 1 | Trans-N-{2-[4-(5-methyl-3-pyridinyl)phenyl]cyclopropyl}-2-propanesulfonamide Enantiomer 1 |
| 19 Enant 2 | 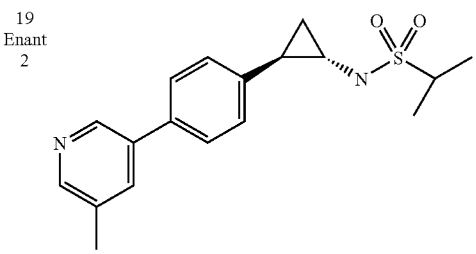 | 331.02 | 329.06 | 77 | 2.52 | 1 | Trans-N-{2-[4-(5-methyl-3-pyridinyl)phenyl]cyclopropyl}-2-propanesulfonamide Enantiomer 2 |
| 20 Enant 2 | 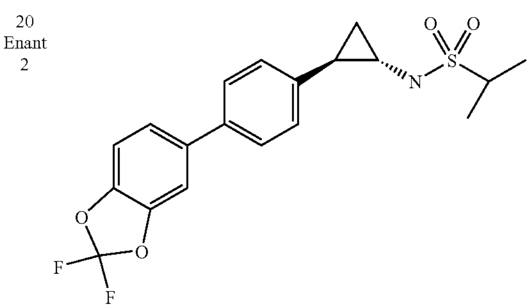 | [412.99] | 393.97 | 94 | 3.83 | 3 | Trans-N-{2-[4-(2,2-difluoro-1,3-benzodioxol-5-yl)phenyl]cyclopropyl}-2-propanesulfonamide Enantiomer 2 |
| 21 Enant 2 | 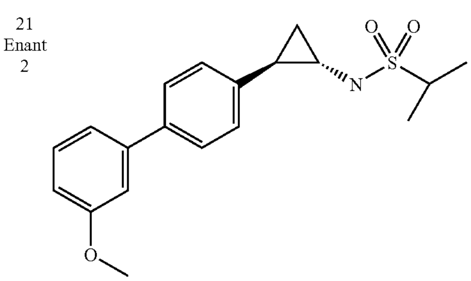 | 346.02, 363.03 | 344.04 | 97 | 3.26 | 2 | Trans-N-{2-[3'-(methyloxy)-4-biphenylyl]cyclopropyl}-2-propanesulfonamide Enantiomer 2 |

TABLE 2-continued

| Ex No | Structure | MS ESI+ MH+ [MNH4+] | MS ESI− (M − H)− | Purity (%) | Ret. Time (min) | Prep. Gradient | Name |
|---|---|---|---|---|---|---|---|
| 22 Enant 1 | 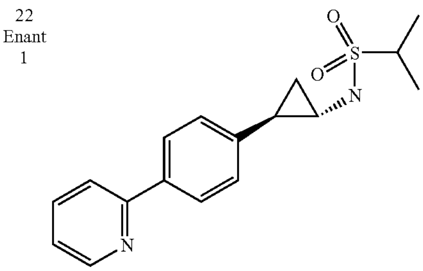 | 316.98 | 315.00 | 81 | 2.1 | 1 | Trans-N-{2-[4-(2-pyridinyl)phenyl]cyclopropyl}-2-propanesulfonamide Enantiomer 1 |
| 22 Enant 2 | 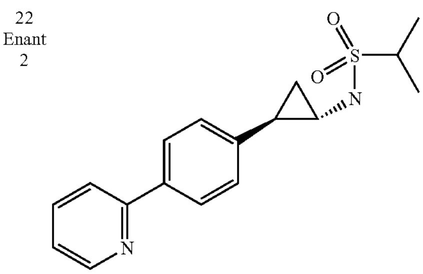 | 316.98 | 315.03 | 89 | 2.1 | 1 | Trans-N-{2-[4-(2-pyridinyl)phenyl]cyclopropyl}-2-propanesulfonamide Enantiomer 2 |
| 23 Enant 2 | 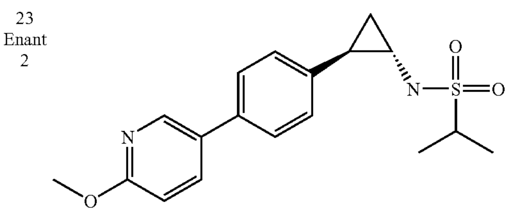 | 347.02 | 345.03 | 75 | 2.74 | 1 | Trans-N-(2-{4-[6-(methyloxy)-3-pyridinyl]phenyl}cyclopropyl)-2-propanesulfonamide Enantiomer 2 |
| 24 Enant 1 | 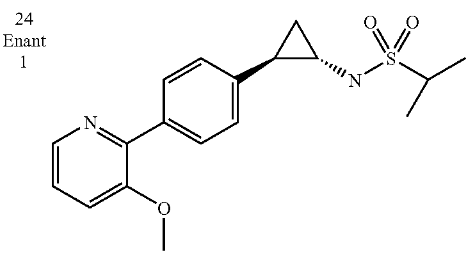 | 347.00 | 345.04 | 90 | 2.06 | 1 | Trans-N-(2-{4-[3-(methyloxy)-2-pyridinyl]phenyl}cyclopropyl)-2-propanesulfonamide Enantiomer 1 |
| 24 Enant 2 | 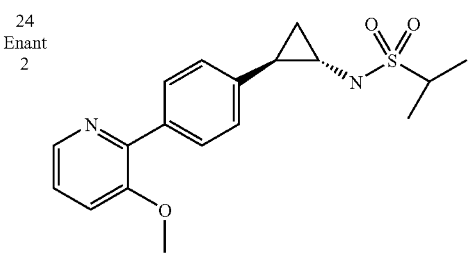 | 347.02 | 345.03 | 85 | 2.06 | 1 | Trans-N-(2-{4-[3-(methyloxy)-2-pyridinyl]phenyl}cyclopropyl)-2-propanesulfonamide Enantiomer 2 |
| 25 Enant 2 | 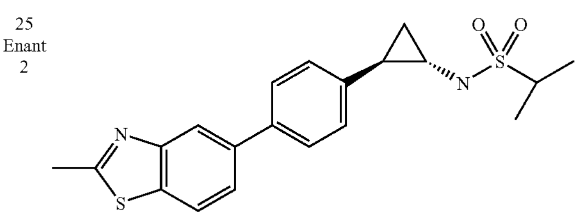 | 387.00 | 385.01 | 84 | 3.13 | 1 | Trans-N-{2-[4-(2-methyl-1,3-benzothiazol-5-yl)phenyl]cyclopropyl}-2-propanesulfonamide Enantiomer 2 |

Biological Assays

The ability of the compounds of the invention to potentiate glutamate receptor-mediated response may be determined a) by using fluorescent calcium-indicator dyes such as FLUO4 and/or b) by measuring glutamate-evoked current recorded from human GluR2 flip unedited HEK293 cells.

a) Calcium Influx Fluorescence Assay 384 well plates were prepared containing confluent monolayer of HEK 293 cells either stably expressing or transiently transfected with human GluR2 flip (unedited) AMPA receptor subunit. These cells form functional homotetrameric AMPA receptors. The tissue culture medium in the wells was discarded and the wells were each washed three times with standard buffer (80 μL) for the stable cell line (145 mM NaCl, 5 mM KCl, 1 mM $MgCl_2$, 2 mM $CaCl_2$, 20 mM N-[2-hydroxyethyl]-piperazine-N-[2-ethanesulfonic acid (HEPES), 5.5 mM glucose, pH 7.3) or with a Na-free buffer for the transient transfected cells (145 mM N-methyl-glucamine instead of NaCl). The plates were then incubated for 60 minutes in the dark with 2 μM FLUO4-AM dye (20 μL) (Molecular Probes, Netherlands) at room temperature to allow cell uptake of the FLUO-4AM, which is then converted to FLUO-4 by intracellular esterases which is unable to leave the cell. After incubation each well was washed three times with buffer (80 μL) (30 μL of buffer remained in each well after washing).

Compounds of the invention (or reference compounds such as cyclothiazide) were dissolved in dimethylsulfoxide (DMSO) at a stock concentration of 10 mM. These solutions were further diluted with DMSO using a Biomek FX (Beckman Coulter) in a 384 compound plate. Each dilution (1 μL) was transferred to another compound plate and buffer (50 μL) was added. An agonist stimulus (glutamate) plate was prepared by dissolving sodium glutamate in water to give a concentration of 100 mM. This solution was diluted with buffer to give a final concentration of 500 μM and dispensed into another 384-well plate (50 μL/well) using a Multidrop (Thermolabsystems).

The cell plate was then transferred into a fluorescence imaging plate based reader [such as the FLIPR384 (Molecular Devices)]. A baseline fluorescence reading was taken over a 10 to 240 second period, and then 10 μL from each plate containing a compound of the invention made up in standard buffer solution (in a concentration range from 100 μM to 10 pM) was added (to give a final concentration in the range 30 μM to 3 pM). The fluorescence was read over 5 minute period. 500 μM glutamate solution (10 μL) was added (to give a final concentration of 100 μM). The fluorescence was then read over a 4 minute period. The activities of the compounds of the invention and reference compounds were determined by measuring peak fluorescence after the last addition. The activity was also expressed relative to the fluorescence increase induced by cyclothiazide at their maximum response (i.e. greater than 30 μM).

The assay described above is believed to have an effective limit of detection of a $pEC_{50}$ in the region of 3.5-4.0 due to the limitations of compound solubility. The $pEC_{50}$ result is generally considered to be accurate +/−0.3. Accordingly, a compound exhibiting a $pEC_{50}$ value within this range from such an assay may indeed have a reasonable affinity for the receptor, but equally it may also have a lower affinity, including a considerably lower affinity.

The Example compounds were screened using the assay as described above and all of the Example compounds except Example 15 Enantiomer 1 gave a $pEC_{50}$ equal to or greater than 3.9 and demonstrated an activity at least 35% that of cyclothiazide (at its maximal response).

b) Whole Cell Voltage-Clamp Electrophysiology Assay

The ability of the compounds of the invention to potentiate AMPA-subtype glutamate receptor-mediated response were determined by measuring AMPA-evoked current recorded from rat cultured hippocampal neurons.

This assay involved the electrophysiological characterisation of AMPA receptor positive modulators using rat cultured hippocampal neurons. The extracellular recording solution contained: 145 mM NaCl, 2.5 mM KCl, 1.2 mM $MgCl_2$, 1.5 mM $CaCl_2$, 10 mM N-[2-hydroxyethyl]-piperazine-N-[2-ethanesulfonic acid (HEPES), 10 mM D-glucose, pH 7.3 with NaOH. The intracellular solution contained: 80 mM CsCl, 80 mM CsF, 10 mM N-[2-hydroxyethyl]-piperazine-N-[2-ethanesulfonic acid (HEPES), 10 mM ethylene glycol-bis(g-aminoethylether)-N,N,N',N-tetra-acetic acid (EGTA), 14 mM MgATP, 14 mM DiTris Creatine Phosphate, 50 U/ml Creatine Phosphokinase pH 7.3 with CsOH. Recording electrodes were prepared from glass capillary tubes (Clark Electromedical GC120-F10) pulled into two equal lengths using a Zeitz Instruments DMZ Universal Puller, program 09, resulting in electrodes with a resistance of approximately 3-6 MOhms when measured in extracellular solution. Electrodes were back filled with internal recording solution. Positive pressure was applied to the electrode to prevent mixture of internal and external solutions and assist in formation of high resistance seal when the electrode makes contact with the cell membrane. Glass coverslip fragment, bearing rat cultured hippocampal neurons, was placed in the recording chamber positioned on the stage of an inverted microscope. A tube at the edge of the chamber was used to apply extracellular solution to the bath. Rapid solution exchange used a fast step perfusion system (Biologic RSC160). Two outlet tubes attached together along their length were positioned close to a chosen cell so that the outflow from only one tube would pass directly over the cell surface. A motorized stepper could re-position the tubes such that the outflow from the second outlet tube flowed over the cell allowing solution exchange at the cell membrane surface to occur within 10-20 ms. Excess bath solution was removed via a tube positioned at the edge of the chamber connected to a vacuum line.

A prospective cell was positioned in the centre of the microscope field of view. Recording electrode was positioned directly above the cell membrane surface. Using fine manipulator control (Luigs and Neumann, SM-6) the electrode was lowered, while monitoring the change in electrode resistance during delivery of a 5 mV depolarizing pulse, until a high resistance seal (gigaseal) was achieved. Whole cell configuration was achieved by removing by suction a small fragment of cell membrane immediately beneath the recording electrode tip. The cell membrane potential was held at −70 mV (voltage-clamped) via the electrode (Axopatch 200B Integrating patch clamp amplifier, pClamp software, Axon Instruments). Test solutions were applied using the fast application system using the following protocol and changes in inward current were recorded and stored for off-line analysis.

1) Control current—exchange from extracellular solution to extracellular solution+30 μM AMPA (2 s application time, 30 s interval between applications) repeated until measurements are stable.

2) Test current—exchange from extracellular solution+10 nM of compound of invention to extracellular solution+10 nM of compound of invention+30 μM AMPA (2 s application time, 30 s interval between applications) repeated until measurements are stable.

All experiments were performed at ambient temperature (20 to 22° C.).

The activity of a compound of the invention is determined by measuring the area under the curve (during 2 s period of application) for the 30 μM AMPA response in the presence of the compound of the invention and expressing it as % of potentiation of the 30 μM AMPA alone response (30 μM AMPA in the absence of the compound of the invention).

Representative compounds of the invention (examples 1, 12 enantiomer 1, 12 enantiomer 2, 15 enantiomer 1 and 15 enantiomer 2) were investigated using the assay with measurements being taken on four neurons. When applied at 10 nM, they increased 30 μM AMPA-mediated currents as follows:

Example 1: from 4 to 42%,

Example 12 enantiomer 1: from 68 to 104%

Example 12 enantiomer 2 from 34 to 114%

Example 15 enantiomer 1 from 10 to 42%

Example 15 enantiomer 2: from 32 to 74%

The variability in the assay results from the heterogenous nature of the subunit populations of the AMPA receptor within different cells.

The invention claimed is:

1. A compound of formula (I), or a salt thereof

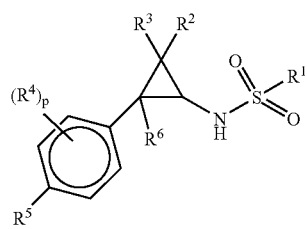

(I)

wherein $R^1$ is selected from $C_{1-6}$alkyl, halo$C_{1-6}$alkyl, $C_{2-6}$alkenyl, amino, mono$C_{1-4}$alkylamino and di$C_{1-4}$alkylamino;

$R^2$, $R^3$ and $R^6$, which may be the same or different, are each independently selected from hydrogen, halogen, $C_{1-6}$alkyl, halo$C_{1-6}$alkyl and $C_{1-4}$alkoxy;

each $R^4$, which may be the same or different, is selected from $C_{1-6}$alkyl, halogen, halo$C_{1-6}$alkyl, $C_{1-4}$alkoxy, halo$C_{1-4}$alkoxy and cyano;

p is selected from 0, 1 and 2; and $R^5$ is phenyl or an aromatic heterocyclyl, either of which is optionally substituted with one or more groups Y;

each Y group is independently selected from the group consisting of:

$C_{1-6}$alkyl, halogen, halo$C_{1-6}$alkyl, $C_{1-4}$alkoxy, halo$C_{1-4}$alkoxy, cyano, $-(CH_2)_qNR^{5a}SO_2R^{5b}$, $-(CH_2)_qNR^{5a}(C=O)R^{5d}$, $-(CH_2)_qNR^{5a}(C=O)N(R^{5c})_2$, $-(CH_2)_q(C=O)R^{5d}$, $-(CH_2)_qSO_2R^{5b}$; where $R^{5a}$ and each $R^{5c}$, which may be the same or different, is selected from hydrogen and $C_{1-6}$alkyl; $R^{5b}$ is selected from $C_{1-6}$alkyl and halo$C_{1-6}$alkyl; $R^{5d}$ is selected from $C_{1-6}$alkyl, $C_{1-4}$alkoxy and halo$C_{1-6}$alkyl; or $R^{5a}$ and $R^{5b}$, $R^{5a}$ and $R^{5c}$, or $R^{5a}$ and $R^{5d}$, where appropriate, together with the interconnecting atoms, may form a 5- or 6-membered ring; and q is 0, 1, or 2; in the case when there are two or more Y groups present, two of them together may form a cyclic group selected from $-(CH_2)_rOR^{5e}O(CH_2)_s-$ and $-(CH_2)_rOR^{5e}-$ where $R^{5e}$ is a group selected from $C_{1-4}$alkylene or halo $C_{1-4}$alkylene; r and s are each independently 0, 1 or 2; and t is 2 or 3.

2. A compound of formula (I), or a salt thereof according to claim 1 wherein $R^1$ is $C_{1-6}$ alkyl.

3. A compound of formula (I), or a salt thereof according to claim 1 wherein $R^2$, $R^3$ and $R^6$, which may be the same or different, are hydrogen, halogen or $C_{1-6}$ alkyl.

4. A compound of formula (I), or a salt thereof according to claim 1 wherein $R^2$ and $R^3$ are hydrogen and $R^6$ is hydrogen, halogen or methyl.

5. A compound of formula (I), or a salt thereof according to claim 1 wherein, when present, each $R^4$, which may be the same or different, is $C_{1-6}$ alkyl or halogen.

6. A compound of formula (I), or a salt thereof according to claim 1 wherein p is 0.

7. A compound of formula (I), or a salt thereof according to claim 1 wherein each Y group is independently selected from the group consisting of: $C_{1-6}$alkyl, halogen, halo$C_{1-6}$alkyl, $C_{1-4}$alkoxy, halo$C_{1-4}$alkoxy, cyano, $-(CH_2)_qNR^{5a}SO_2R^{5b}$, $-(CH_2)_qNR^{5a}(C=O)R^{5d}$, $-(CH_2)_qNR^{5a}(C=O)N(R^{5c})_2$, $-(CH_2)_q(C=O)R^{5d}$ and $-(CH_2)_qSO_2R^{5b}$; where $R^{5a}$ and each $R^{5c}$, which may be the same or different, is hydrogen or $C_{1-6}$alkyl; $R^{5b}$ is $C_{1-6}$alkyl or halo$C_{1-6}$alkyl; $R^{5d}$ is $C_{1-6}$alkyl, $C_{1-4}$alkoxy or halo$C_{1-6}$alkyl; or $R^{5a}$ and $R^{5b}$, $R^{5a}$ and $R^{5c}$, or $R^{5a}$ and $R^{5d}$, where appropriate, together with the interconnecting atoms, may form a 5- or 6-membered ring; and q is 0, 1, or 2.

8. A compound of formula (I), or a salt thereof according to claim 1 wherein $R^5$ is selected from phenyl, pyridyl, pyrazinyl, pyrimidinyl, pyridazinyl, imidazolyl, pyrroyl, oxazolyl, thienyl, thiadiazolyl, benzothiazolyl, benzofuranyl, benzimidazolyl and pyrazolyl, optionally substituted by one or more groups Y.

9. A compound of formula (I), or a salt thereof according to claim 1 wherein $R^5$ is selected from phenyl, pyridyl, thienyl and benzthiazolyl, optionally substituted by one or more groups Y.

10. A compound of formula (I), or a salt thereof according to claim 1 wherein $R^5$ is phenyl, optionally substituted by one or more groups Y independently selected from $-(CH_2)_qNR^{5a}SO_2R^{5b}$, $-(CH_2)_qNR^{5a}(C=O)R^{5d}$, $-(CH_2)_qNR^{5a}(C=O)N(R^{5c})_2$, $-(CH_2)_q(C=O)R^{5d}$ and $-(CH_2)_qSO_2R^{5b}$; where $R^{5a}$ and each $R^{5c}$, which may be the same or different, is hydrogen or $C_{1-6}$alkyl; $R^{5b}$ is $C_{1-6}$alkyl or halo$C_{1-6}$alkyl; $R^{5d}$ is $C_{1-6}$alkyl, $C_{1-4}$alkoxy or halo$C_{1-6}$alkyl; or $R^{5a}$ and $R^{5b}$, $R^{5a}$ and $R^{5c}$, or $R^{5a}$ and $R^{5d}$, where appropriate, together with the interconnecting atoms, may form a 5- or 6-membered ring; and q is 0, 1, or 2, which may be the same or different.

11. A compound of formula (I), or a salt thereof according to claim 1 wherein Y is selected from $C_{1-4}$ alkyl and halogen.

12. A compound of formula (I), or a salt thereof according to claim 1 wherein the compound is of formula (Ia) in which the sulphonamide and phenyl substituents on the cyclopropyl ring are in a trans arrangement relative to each other:

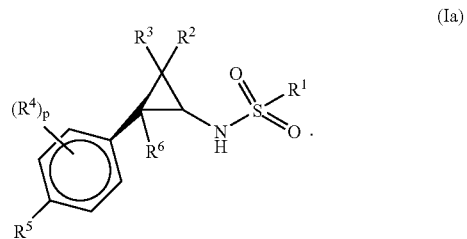

(Ia)

13. A pharmaceutical composition comprising the compound of claim 1 or a pharmaceutically acceptable salt thereof and at least one pharmaceutically acceptable carrier or diluent.

14. A combination product comprising a compound of formula (I), or a pharmaceutically acceptable salt thereof according to claim 1 with an antipsychotic.

15. A compound according to claim 1 or a salt thereof which is:

trans-N-{-2-[4-(6-fluoro-3-pyridinyl)phenyl]cyclopropyl}-2-propanesulfonamide;

trans-N-{-2-[4-(6-methyl-3-pyridinyl)phenyl]cyclopropyl}-2-propanesulfonamide;

trans-N-{-2-[4-(5-fluoro-2-pyridinyl)phenyl]cyclopropyl}-2-propanesulfonamide;

trans-N-{-2-[4-(5-chloro-2-pyridinyl)phenyl]cyclopropyl}-2-propanesulfonamide;

trans-N-{-2-[4-(5-fluoro-phenyl)phenyl]cyclopropyl}-2-propanesulfonamide;

trans-N-{-2-[4-(4-cyano-phenyl)phenyl]cyclopropyl}-2-propanesulfonamide;

trans-N-{(2-[4-(1,3-benzodioxol-5-yl)phenyl]cyclopropyl}-2-propanesulfonamide;

trans-N-{-2-[3-(thienyl)phenyl]cyclopropyl}-2-propanesulfonamide;

trans-N-{-2-[2-(thienyl)phenyl]cyclopropyl}-2-propanesulfonamide;

trans-N-{-2-[4-(5-fluoro-3-pyridinyl)phenyl]cyclopropyl}-2-propanesulfonamide;

trans-N-{-2-[4-(5-methyl-3-pyridinyl)phenyl]cyclopropyl}-2-propanesulfonamide;

trans-N-{2-[4-(5-fluoro-3-pyridinyl)phenyl]cyclopropyl}-2-propanesulfonamide enantiomer 1;

trans-N-{2-[4-(5-fluoro-3-pyridinyl)phenyl]cyclopropyl}-2-propanesulfonamide enantiomer 2;

trans-N-{2-[4-(6-fluoro-3-pyridinyl)phenyl]cyclopropyl}-2-propanesulfonamide Enantiomer 1;

trans-N-{2-[4-(6-fluoro-3-pyridinyl)phenyl]cyclopropyl}-2-propanesulfonamide Enantiomer 2;

trans-N-{2-[4-(5-fluoro-2-pyridinyl)phenyl]cyclopropyl}-2-propanesulfonamide Enantiomer 1;

trans-N-{2-[4-(5-fluoro-2-pyridinyl)phenyl]cyclopropyl}-2-propanesulfonamide Enantiomer 2;

trans-N-{2-[4-(5-chloro-2-pyridinyl)phenyl]cyclopropyl}-2-propanesulfonamide Enantiomer 1;

trans-N-{2-[4-(5-chloro-2-pyridinyl)phenyl]cyclopropyl}-2-propanesulfonamide Enantiomer 2;

trans-N-[2-(4'-fluoro-4-biphenylyl)cyclopropyl]-2-propanesulfonamide Enantiomer 1;

trans-N-[2-(4'-fluoro-4-biphenylyl)cyclopropyl]-2-propanesulfonamide Enantiomer 2;

trans-N-[2-(4'-cyano-4-biphenylyl)cyclopropyl]-2-propanesulfonamide Enantiomer 1;

trans-N-{2-[4-(1,3-benzodioxol-5-yl)phenyl]cyclopropyl}-2-propanesulfonamide Enantiomer 2;

trans-N-{2-[4-(5-methyl-3-pyridinyl)phenyl]cyclopropyl}-2-propanesulfonamide Enantiomer 1;

trans-N-{2-[4-(5-methyl-3-pyridinyl)phenyl]cyclopropyl}-2-propanesulfonamide Enantiomer 2;

trans-N-{2-[4-(2,2-difluoro-1,3-benzodioxol-5-yl)phenyl]cyclopropyl}-2-propanesulfonamide Enantiomer 2;

trans-N-{2-[3'-(methyloxy)-4-biphenylyl]cyclopropyl}-2-propanesulfonamide Enantiomer 2;

trans-N-{2-[4-(2-pyridinyl)phenyl]cyclopropyl}-2-propanesulfonamide Enantiomer 1;

trans-N-{2-[4-(2-pyridinyl)phenyl]cyclopropyl}-2-propanesulfonamide Enantiomer 2;

trans-N-(2-{4-[6-(methyloxy)-3-pyridinyl]phenyl}cyclopropyl)-2-propanesulfonamide Enantiomer 2;

trans-N-(2-{4-[3-(methyloxy)-2-pyridinyl]phenyl}cyclopropyl)-2-propanesulfonamide Enantiomer 1;

trans-N-(2-{4-[3-(methyloxy)-2-pyridinyl]phenyl}cyclopropyl)-2-propanesulfonamide Enantiomer 2; or trans-N-{2-[4-(2-methyl-1,3-benzothiazol-5-yl)phenyl]cyclopropyl}-2-propanesulfonamide Enantiomer 2.

* * * * *